United States Patent
Vournakis et al.

(10) Patent No.: US 6,399,328 B1
(45) Date of Patent: Jun. 4, 2002

(54) METHODS AND COMPOSITIONS FOR DIAGNOSIS AND TREATMENT OF BREAST CANCER

(75) Inventors: John N. Vournakis, Charleston, SC (US); Arun K. Seth, Mississauga (CA); Takis S. Papas, Charleston, SC (US)

(73) Assignee: MUSC Foundation For Research Development, Charleston, SC (US)

( * ) Notice: Subject to any disclaimer, the term of this patent is extended or adjusted under 35 U.S.C. 154(b) by 0 days.

(21) Appl. No.: 09/044,781

(22) Filed: Mar. 20, 1998

Related U.S. Application Data

(60) Provisional application No. 60/044,425, filed on Mar. 21, 1997.
(51) Int. Cl.[7] .......................... C12N 5/00; C12N 15/00; C07H 21/02; C07H 21/04; C12Q 1/68
(52) U.S. Cl. ..................... 435/69.1; 536/23.1; 536/23.4; 536/23.5; 536/24.31; 435/6; 435/320.1; 435/325
(58) Field of Search .............................. 536/23.1, 23.4, 536/23.5, 24.31; 514/44; 435/320.1, 325, 252.1, 6, 69.1; 800/8

(56) References Cited

FOREIGN PATENT DOCUMENTS

WO          WO-93/25685        *    6/1993

OTHER PUBLICATIONS

Cameron (Cameron ER. Molecular Biotechnology 7:253–265, 1997.*
Hammer RE et al. Cell 63:1099–1112. 1990.*
Seidel GE. J. Anim. Sci. 71(Suppl. 3):26–33, 1993.*
Mullins JJ et al. Hypertension 22:630–633, 1993.*
Yamauchi T et al. Biochemical Journal 303: 591–598, 1994.*
TM Clay et al., Pathology Oncology Research, "Potential Use of T Cell Receptor Genes to Modify Hematopoietic Stem Cells for the Gene Therapy of Cancer," 1999, vol. 5, No. 1, pp. 3–15.*
IM Verma et al., Nature, "Gene therapy–promises, problems and prospects," Sep. 1997, vol. 389, pp. 239–242.*
J Rudinger, Peptide Hormones, "Characteristics of the amino acids as components of a peptide hormone sequence," Jun. 1976, pp. 1–7.*
CC Liew et al., Locus, Accession No. T12326, 1994.*
T. Fujiwara et al., Locus, Accession No. D57652/c, 1995.*
RB Murphy et al., Geneseq, Accession No. R50800, 1994.*
Abts et al., 1991, "Human Chronic Lymphocytic Leukemia Cells Regularly Express mRNAs of the Protooncogenes Ick and c–fgr", Leuk. Res. 15:987–997.

Allred et al., 1990, "Immunocytochemical Evaluation of HER–2/neu Oncogene Expression in Different Evolutionary Stages of Breast Carcinoma and Correlation with Clinical–Pathological Characteristics", Proc. Am. Soc. Clin. Oncol. 9:23.
Berns et al., 1992, "c–myc Amplification is a Better Prognostic Factor than HER2/neu Amplification in Primary Breast Cancer", Cancer Res. 52:1107–1113.
Burger et al., 1998, "Breast Cancer Genome Anatomy: Correlation of Morphological Changes in Breast Carcinomas with Expression of the Novel Gene Product Di12", Oncogene 16:327–333.
Burger et al., 1997, "Dissection of Breast Cancer Genome Anatomy", Breast Cancer Res. and Treat. 46:28.
Burger et al., 1996, "Identification of Differentially Expressed Genes in Breast Cancer", Int'l J. Oncol. 8:395–400.
Burger et al., 1996, "Analysis of DIT1A12 Gene Product in Sera and Tissue of Breast Cancer Patients", Proc. Am. Assoc. Cancer Res. Ann. Mtg. 37(0):572.
Easton et al., 1993, "Inherited Susceptibility to Breast Cancer", Cancer Surveys 18:95–113.
Iwase et al., 1994, "Evaluation of Serum Tumor Markers in Patients with Advanced or Recurrent Breast Cancer", Breast Cancer Res. and Treat. 33:83–88.
Liang and Pardee, 1992, "Differential Display of Eukaryotic Messenger RNA by Means of the Polymerase Chain Reaction", Science 257:967–971.
Miki et al., 1994, "A Strong Candidate for the Breast and Ovarian Cancer Susceptibility Gene BRCA1", Science 266:66–71.
Morgan and Anderson, 1993, "Human Gene Therapy", Annu. Rev. Biochem. 62:191–217.
Murre et al., 1989, "A New DNA Binding and Dimerization Motif in Immunoglobulin Enhancer Binding, daughterless, MyoD, and myc Proteins", Cell 56:777–783.

(List continued on next page.)

*Primary Examiner*—Dave T. Nguyen
*Assistant Examiner*—Ram R. Shukla
(74) *Attorney, Agent, or Firm*—Pennie & Edmonds LLP

(57) ABSTRACT

The present invention relates to a novel gene, Di12, that is differentially expressed as a 1.35 kb RNA in breast cancer tissues and cell lines, and in several normal tissues. The full length cDNA encodes a protein of 339 amino acids. Antibodies to the gene product were developed to investigate the expression of Di12 in breast cancer cell-lines and tumors. The Di12 protein was found in tissue sections of infiltrating ductal carcinomas (IDCs), but not in benign or normal breast specimens. Di12 wag also present in IDC-breast cancer patient sera, and its expression level increased markedly if IDC was accompanied by lymph node or distal metastases. As IDC constitutes ~70% of breast cancers seen clinically, the level of Di12 expression is useful for diseases diagnosis predicting disease progression and monitoring a therapeutic treatment.

23 Claims, 11 Drawing Sheets

OTHER PUBLICATIONS

Figure 2:
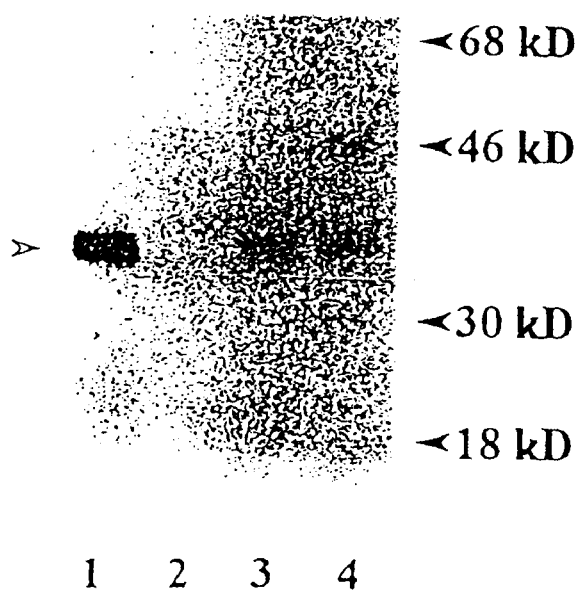

Norton et al., 1995, "Refining the Origins of Breast Cancer", Nature Med. 1:1250–1251.

Rossi, 1994, "Making Ribozymes Work in Cells", Curr. Biol. 4:469–471.

Sainsbury et al., 1987, "Epidermal–Growth–Factor Receptor Status as Predictor of Early Recurrence of and Death from Breast Cancer", The Lancet 1:1398–1402.

Salesiotis et al., 1995, "Identification of Novel Genes from Stomach Cancer Cell Lines by Differential Display", Cancer Lett. 91:47–54.

Schweinfest et al., 1990, "Subtraction Hybrization cDNA Libraries from Colon Carcinoma and Hepatitc Cancer", Genet. Annal. Techn. 7:64–70.

Shimasaki et al., 1991, "Identification of Five Different Insulin–Like Growth Factor Binding Proteins (IGFBP'S) from Adult Rat Serum and Molecular Cloning of a Novel IGFBP–5 in Rat and Human", J. Biol. Chem. 266:10646–10653.

Tavtigian et al., 1996, "The Complete BRCA2 Gene and Mutations in Chromosome 13q–Linked Kindreds", Nature Genetics 12:333–337.

Wagner, 1994, "Gene Inhibition Using Antisense Oligodeoxynucleotides", Nature 372:333–335.

Burger et al., 1997, "A Novel Membrane Protein Associated with Late State Breast Cancer", Protein Engineering. 10 (Suppl.):80.

Burger et al:, 1998, "Breast Cancer Associate Gene Di12 Confers Mammary Tumor Formation in Nude Mice", 89th Annual Meeting of the American Association for Cancer Research, Proceedings of the American Association for Cancer Research Annual Meeting. 39:273 Abstract 1868.

GenBank Accession No. Z16011, HSA56G072 CLONTECH cDNA library CCRF–CEM, cat# HL 1063g Homo sapiens cDNA clone 56G07, mRNA sequence; Entry created: Sep. 15, 1992; Last Updated: Aug. 21, 1998.

GenBank Accession No. Z15500, HSA23D012 CLONTECH cDNA library CCRF–CEM, cat# HL 1063g Homo sapiens cDNA clone 23D01, mRNA sequence; Entry created: Sep. 15, 1992; Last Updated: Aug. 21, 1998.

GenBank Accession No. Z15555, HSA27A032 CLONTECH cDNA library CCRF–CEM, cat# HL 1063g Homo sapiens cDNA clone 27A03, mRNA sequence; Entry created: Sep. 15, 1992; Last Updated: Aug. 21, 1998.

GenBank Accession No. Z13711, HSA68F071 CLONTECH cDNA library CCRF–CEM, cat# HL 1063g Homo sapiens cDNA clone 68F07, mRNA sequence; Entry created: Sep. 15, 1992; Last Updated: Aug. 21, 1998.

GenBank Accession No. Z13717, HSA69C041 CLONTECH cDNA library CCRF–CEM, cat# HL 1063g Homo sapiens cDNA clone 69C04, mRNA sequence; Entry created: Sep. 15, 1992; Last Updated: Aug. 21, 1998.

GenBank Accession No. Z13677, HSA65D041 CLONTECH cDNA library CCRF–CEM, cat# HL 1063g Homo sapiens cDNA clone 65D04, mRNA sequence; Entry created: Sep. 15, 1992; Last Updated: Aug. 21, 1998.

GenBank Accession No. Z13104, HSA25H071 CLONTECH cDNA library CCRF–CEM, cat# HL 1063g Homo sapiens cDNA clone 25H07, mRNA sequence; Entry created: Sep. 15, 1992; Last Updated: Aug. 21, 1998.

GenBank Accession No. Z12846, HSA08C081 CLONTECH cDNA library CCRF–CEM, cat# HL 1063g Homo sapiens cDNA clone 08C08, mRNA sequence; Entry created: Sep. 15, 1992; Last Updated: Aug. 21, 1998.

* cited by examiner

1    MARDGASIKTIKSEFPAIAQAATAAGADLQQTASVVQQSMNIWGDSIQSPQRAAAVLTQT

61   ANLSNASIEDMQQALATIGGTAHNAGIDMQTTSTAIGLLTNRGFSAAQASQDLNHALLLM

121  QAPSEKGAGVMHNLGLSNTDAQGNMKPLPKILNEIGDATRGMTSSDKAAALKAMFGTAGM

181  AAILPLMDSVKDKTGNATTSWEAFTKEMDKASGSTQTATNFLKDQANEMQKNLGSKIEQV

241  GGNWEALSNKAMAGSSGVTGAFLDMTNSALSWAGSNSSMAQFSRQMLGLAPAIGPVVTA

301  LGGFITNAGKITGLVKGMGSAVIGAGKGMVSFVAFFFFV

*Fig. 1A*

```
   1  gggtggagacttccaagcgtcacttaaccaagccgcagtcatcgctggtggtacatcaaa
  61  agacattaacggacttgctgacgtagccaacaaaatgggtgctgacctgcctttaagcgc
 121  tggtgctgctgcgaaagctatggtagccatggctcgtgacggagcgtctatcaagacaat
 181  taaatcagagttcccagctattgcgcaagctgcaacggctgctggtgctgatttgcagca
 241  aacagcgtcagttgttcaacaatcgatgaacatctggggtgatagtattcaaagcccaca
 301  acgtgctgctgctgtattaacgcaaactgctaacctatccaacgcctcaatcgaagatat
 361  gcaacaggctttagctactatcggtggtacggcacacaacgctggtatcgacatgcaaac
 421  aacgtctaccgctatcggtttacttactaaccgtggtttcagtgctgcacaagcgtcaca
 481  agacttgaaccatgctttgttgctcatgcaagctccaagtgaaaaaggagctggtgtgat
 541  gcacaatctcggtttgtctatgacagacgcacaaggaaacatgaagccgttaccaaaaat
 601  tttgaatgaaattggtgacgcgacacgtgggatgactagttctgataaagcagcagcgtt
 661  gaaggctatgtttggtactgctggtatggctgctattcttcctttgatggatagtgtcaa
 721  ggataagactggtaatgctaccacaagttgggaagctttcaccaaagaaatggataaagc
 781  gtcaggaagtacgcaaacagctacaaacttcctaaaagatcaagcaaacgaaatgcagaa
 841  aaacttgggttctaagatcgaacaagtcggtggtaactgggaagcattaagcaacaaggc
 901  tatggctggatcttctggtgtcactggtgcgttccttgacatgacaaatagcgcattaag
 961  ttgggctggttctagtaatagttcaatggcacagttttcacgtcaaatgcttggtttagc
1021  accagctatcgggccagttgttactgctttgggtggatttattaccaacgctgggaagat
1081  tactggactggtaaaaggtatgggttcagcagttattggtgctggtaagggaatggttag
1141  ttttgttgcttttttttttctttgtgtaaaaccagtgaatataactaaagtgttagtggat
1201  tggattaaaagaaacttattaggcaagaacaggtaatgtagttatccatgactacttta
1261  accatgcagactaataatattctggaggtttatagctcggcaccttcaccttttttcact
1321  ggtatttcatgtaaggcatcaaccactgtgaaaaaaaaaaaaaaaaaaaaaaaa         1374
```

*Fig. 1B*

|       |       |       |
|-------|-------|-------|
| HTB-26 | Hs578T | BT-20 |

◂ 1.35 kb 1   2   3

◂ 28s

◂ 18s 1   2   3

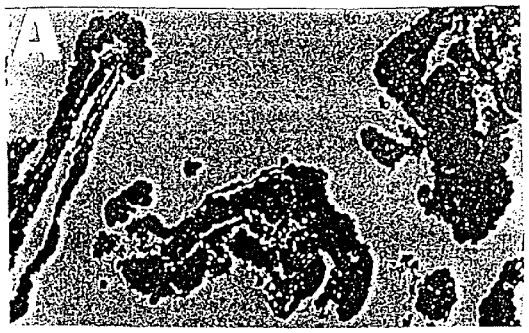
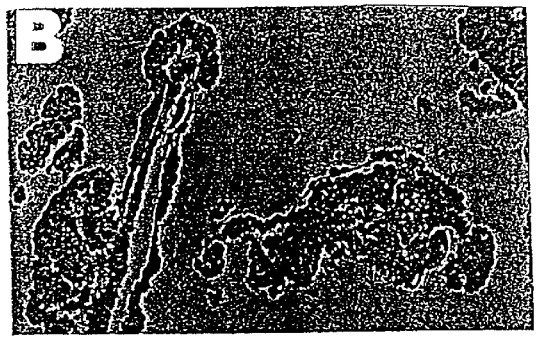
*Fig. 4A*      *Fig. 4B*
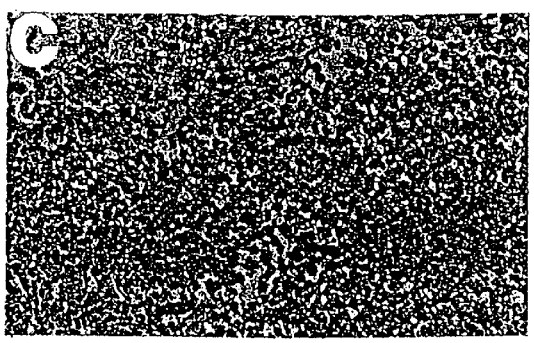
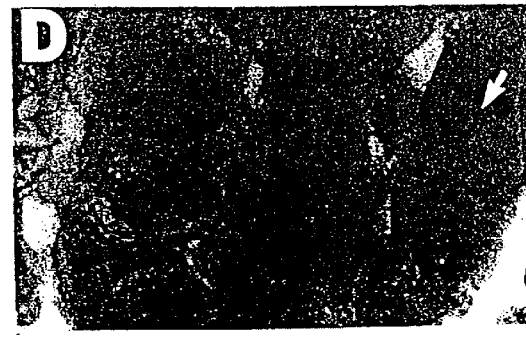
*Fig. 4C*      *Fig. 4D*

METHODS AND COMPOSITIONS FOR DIAGNOSIS AND TREATMENT OF BREAST CANCER

This application claims the benefit of U.S. Provisional Application No. 60/044,425, filed Mar. 21, 1997.

1. INTRODUCTION

The present invention relates to the discovery, identification and characterization of nucleotides that encode Di12, a protein that is overexpressed in breast cancer tissue. The invention encompasses Di12 nucleotides, host cell expression systems, Di12 proteins, fusion proteins, polypeptides and peptides, antibodies to the gene product, transgenic animals that express an Di12 transgene, or recombinant knock-out animals that do not express the Di12, and other compounds that modulate Di12 gene expression or Di12 activity that can be used for diagnosis, disease monitoring, drug screening, and/or the treatment of cancer disorders, including but not limited to breast cancer.

2. BACKGROUND

Cancer is characterized primarily by an increase in the number of abnormal cells derived from a given normal tissue, invasion of adjacent tissues by these abnormal cells, and lymphatic or blood-borne spread of malignant cells to regional lymph nodes and to distant sites (metastasis). Clinical data and molecular biologic studies indicate that cancer is a multistep process that begins with minor pre-neoplastic changes, which may under certain conditions progress to neoplasia.

Pre-malignant abnormal cell growth is exemplified by hyperplasia, metaplasia, or most particularly, dysplasia (for review of such abnormal growth conditions, see Robbins & Angell, 1976, Basic Pathology, 2d Ed., W.B. Saundorg Co., Philadelphia, pp. 68–79.) The neoplastic lesion may evolve clonally and develop an increasing capacity for growth, metastasis, and heterogeneity, especially under conditions in which the neoplastic cells escape the host's immune surveillance (Roitt, I., Brostoff, J and Kale, D., 1993, Immunology, 3rd ed., Mosby, St. Louis, pps. 17.1–17.12).

Breast cancer is the most common form of malignancy in women. One in nine women in North America will develop breast cancer and about 30% of them will ultimately die from the disease (Boring et al., 1993, Cancer Statistics, CA-A Journal for Physicians, 43:7–26). The American Cancer Society estimated that in 1992 180,000 American women were diagnosed with breast cancer and 46,000 succumbed to the disease (Niederhuber, J. E. ed. Current Therapy in Oncology B. C. Decker, Mosby, 1993). A disturbing fact is the observation that breast cancer has been increasing at a rate of 3 percent per year since 1980 (Niederhuber, J. E., ed. Current Therapy in Oncology, B. C. Decker, Mosby, 1993).

The natural history of breast cancer is characterized by a long duration and marked heterogeneity within and among patients. Breast cancer is among the more slow-growing tumors, and the preclinical period before diagnosis and the clinical phases after initial treatment and even after the appearance of metastasis are measured in years and decades. Nevertheless, some patients have aggressive forms of the disease and do poorly. Other patients have such indolent forms of the disease that it is difficult to demonstrate that therapy has any effect on survival. During the long clinical phase, there is ample opportunity for clonal mutation and evolution, and it seems probable that individual patients may have multiple tumor clones, each with its own growth rate, propensity to metastasize, and sensitivity to drugs.

In both Europe and North America, early detection campaigns based on mass screening programs have been introduced in an effort to reduce mortality rates. Widespread use of these procedures has resulted in an increased frequency of detection of breast cancer, which in turn has contributed to a greater number of women with early stage disease (Harris et al., 1993, Cancer: Principles and Practice of Oncology, eds. De Vita, V. T., Hellman, S., & Rosenberg, S. A. (J.B. Lippincott, Philadelphia), 4th Ed., pp. 1264–232). Given the high degree of morphological heterogeneity of most breast cancers, it is at present still difficult to assess appropriate therapy and risk of recurrence for the majority of women-who present with early stage disease. The currently available criteria affecting prognosis are tumor size and grade, lymph node status, DNA ploidy and mitotic index, lymphovascular invasion, as well as estrogen receptor status (Harris et al., 1993, Cancer: Principles and Practice of Oncology, eds. De Vita, V. T., Hellman, S., & Rosenberg, S. A., J.B. Lippincott, Philadelphia, 4th Ed., pp. 1264–1332). These multiple parameters remain poorly correlated with the molecular events associated with a multi-step progression of malignancy, e.g., it has been recently well defined for colorectal cancers (Vogelstein et al., 1993, Trends in Genetics, 9:138–141; Kinzler et al., 1996, Cell, 87:159–170).

The recent discoveries that individuals with BRCA1 and BRCA2 mutations have a predisposition to breast cancer may now facilitate the detection of an early onset type disease for hereditary breast cancer (Easton et al., 1993, Cancer Surv, 18:95–1131; Miki et al., 1994, Science, 266:66–71; Tavtigian et al., 1994, Nature Gen, 12:333–337). The incidence of these cases however, is just 5–10% of all known breast cancers (Easton et al., 1993, Cancer Surv, 18:95–1131; Miki et al., 1994, Science, 266:66–71; Tavtigian et al., 1994, Nature Gen, 12:333–337). Thus, early and late stage specific tumor markers are desperately needed for more than 90% of sporadic forms of breast malignancies.

Tumor suppressor genes and oncogenes play critical roles in the development of malignancies. Amplification and activation of several oncogenes in primary breast tissues such as c-erb-b2 (HER-2/neu), c-MYC and INT2, have been previously implicated and subsequently evaluated for their prognostic potential (Allred et al., 1990, Proc Am Soc Clin Oncol, 9:23; Berns et al., 1992, Cancer Res., 52:1107–1113). Molecular factors such as growth factor receptors and hormone induced genes have also been investigated (Sainsbury et al., 1987, Lancet, 1:1398–1402; Iwase et al., 1994, Breast Cancer Res Treat, 33:83–88). Unfortunately, the expression of these genes is often limited to a small percentage of breast carcinomas only, and their predictive prognostic value remains unclear. The need for markers which would discriminate biological differences between primary and metastatic breast tumors and provide early diagnosis remains pressing. Such factors would assist in identifying individuals at risk for aggressive disease, and aid therapeutic decisions.

3. SUMMARY OF THE INVENTION

The present invention relates to the identification of novel genes whose expression pattern is upregulated in breast cancer tissues and cell lines, and the use of such genes and gene products as targets for diagnosis, drug screening and therapies.

In particular, the compositions of the present invention include nucleic acid molecules that encode the novel Di12 protein, including recombinant DNA molecules, cloned genes or degenerate variants thereof, especially naturally occurring variants which encode novel Di12 gone products. The compositions of the present invention additionally include cloning vectors, including expression vectors, containing the nucleic acid molecules of the invention and hosts which contain such nucleic acid molecules. The compositions of the present invention also encompass the Di12 gene products, fusion proteins, and antibodies directed against such Di12 gene products or conserved variants or fragments thereof.

The nucleic acid sequence of the human Di12 gene (SEQ ID NO:1) is provided. The Di12 gene produces a transcript of approximately 1.35 kb and encodes a protein of 339 amino acids with a molecular weight of approximately 35 kD. Transcripts were detected in several breast cancer cell lines, as well as various normal tissues, including lung, kidney, pancreas and heart. The amino acid sequence of the predicted full length Di12 gene product does not contain a recognizable signal sequence, indicating that the Di12 gene product is an intracellular protein.

The present invention further relates to methods for the diagnostic evaluation and prognosis of breast cancer. For example, nucleic acid molecules of the invention can be used as diagnostic hybridization probes or as primers for diagnostic PCR analysis for detection of abnormal expression of the Di12 gene.

Antibodies to Di12 gene product of the invention can be used in a diagnostic test to detect the presence of Di12 gene product in body fluids. In specific embodiments, measurement of serum or plasma Di12 gene product levels can be made to detect or stage breast cancer, especially infiltrative ductal carcinoma.

The present invention also relates to methods for the identification of subjects having a predisposition to breast cancer. For example, nucleic acid molecules of the invention can be used as diagnostic hybridization probes or as primers for diagnostic PCR analysis for the identification of Di12 gene mutations, allelic variations and regulatory defects in the Di12 gene.

Further, methods and compositions are presented for the treatment of breast cancer. Such methods and compositions are capable of modulating the level of Di12 gene expression and/or the level of Di12 gene product activity.

Still further, the present invention relates to methods for the use of the Di12 gene and/or Di12 gene products for the identification of compounds which modulate Di12 gene expression and/or the activity of Di12 gene products. Such compounds can be used as agents to prevent and/or treat breast cancer. Such compounds can also be used to palliate the symptoms of the disease, and control the metastatic potential of breast cancer.

4. BRIEF DESCRIPTION OF THE FIGURES

FIGS. 1A–B. FIG. 1A. The predicted amino acid sequence of Di12 protein (SEQ ID NO: 1). The 12 N-terminal amino acids used for generating antibodies are italicized, N-glycosylation sites are boxed, PKC sites are bold, and CKU sites are underlined. FIG. 1B. The complementary DNA (cDNA) sequence encoding Di12 (SEQ ID NO: 2). The initiation codon is underlined and the termination codon is boxed.

FIG. 2. Immunoprecipitation of Di12 expressed using an in vitro expression system. $^{35}$S-Met labeled Di12 protein was synthesized in vitro using the TnT kit (Promega) and immunoprecipitated with Di12 specific antibodies (Lanes 3 and 4) or preimmune serum (Lane 2). Lane 1 contains in vitro translated Di12 protein.

FIGS. 3A–G. Expression of Di12 in breast cancer cell lines and normal tissues. RNA from breast cancer cell lines (FIG. 3A and 3C) and normal human (FIG. 3E) and rat tissues (FIG. 3F) were analyzed by Northern hybridization with a Di12 probe. 1.35 kb Di12 specific RNA is indicated by arrows in each panel. Ethidium bromide stained agarose gels before blotting are shown below each autoradiogram (FIG. 3B, 3D and 3G) except for normal human tissues where a poly-A blot from Clonetech was used. Names of cell lines and tissues are indicated above each lane.

FIGS. 4A–H: Immunohistochemical analysis of Di12 expression

FIGS. 4A–D. Analysis of paraffin embedded cell preparations from breast cancer cell lines using Di12 antibody: BT-483, FIG. 4A (150×), FIG. 4D (1000×). Hs578T, FIG. 4C (150×). FIG. 4B is a negative control for A. BT-483 cells probed with rat immunoglobulins show only hematoxylin stain, FIG. 4B (150×). Interestingly the appearance of BT 483 (origin: infiltrative ductal carcinoma) cell architecture is tubular papillary-like, although without stromal support.

Figure 4E:
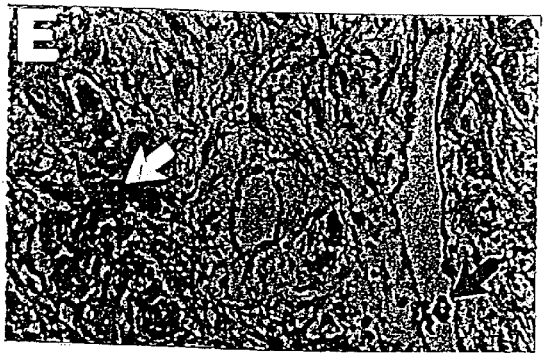

FIGS. 4E–H. Di12 protein expression in breast tissues using Di12 antibody. Invasive ductal carcinoma, IDC (no special type, NST), grade IH, probed with Di12 antibody, immunoperoxidase staining, FIG. 4E (magnification 150×). Strands of infiltrating, pleomorphic cells (white→) and areas of vascular space invasion (black→) stain strongly positive. Enlargement of Di12 positive cells from FIG. 4E shows diffused cytoplasmic staining with a slight increase of stain in perinuclear regions (white→), FIG. 4F (1000×). IDC (NST), grade U, with retraction artifacts (space around islands of cells). Rounded cohesive islands of malignant cells show intensive cytoplasmic staining. Cells are only mildly pleomorphic with some tubular differentiation, FIG. 4G (150×). Normal breast tissue (from breast reduction) probed with Di12 antibody, showing normal appearance of a lobule with no specific peroxidase staining FIG. 4H (150×).

Figure 5:
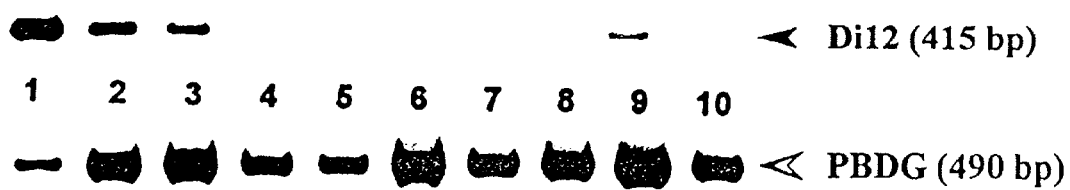

FIG. 5. Expression of. Di12 in nominal and breast cancer tissue samples. RT-PCR of identical cDNA samples from various nominal and benign breast tissues were carried out with Di12 specific primers (top) and the housekeeping gene, porphobilinogen deaminase (bottom). PCP amplified products were analyzed on a 2% agarose gel. Lanes 1, 2, 3, and 9 contain IDC samples. Lane 6 contains intraductal papilloma sample, lane 4 contains benign tissue and samples in lanes 7, 8 and 10 are derived from fibroadenomas.

Figure 6:
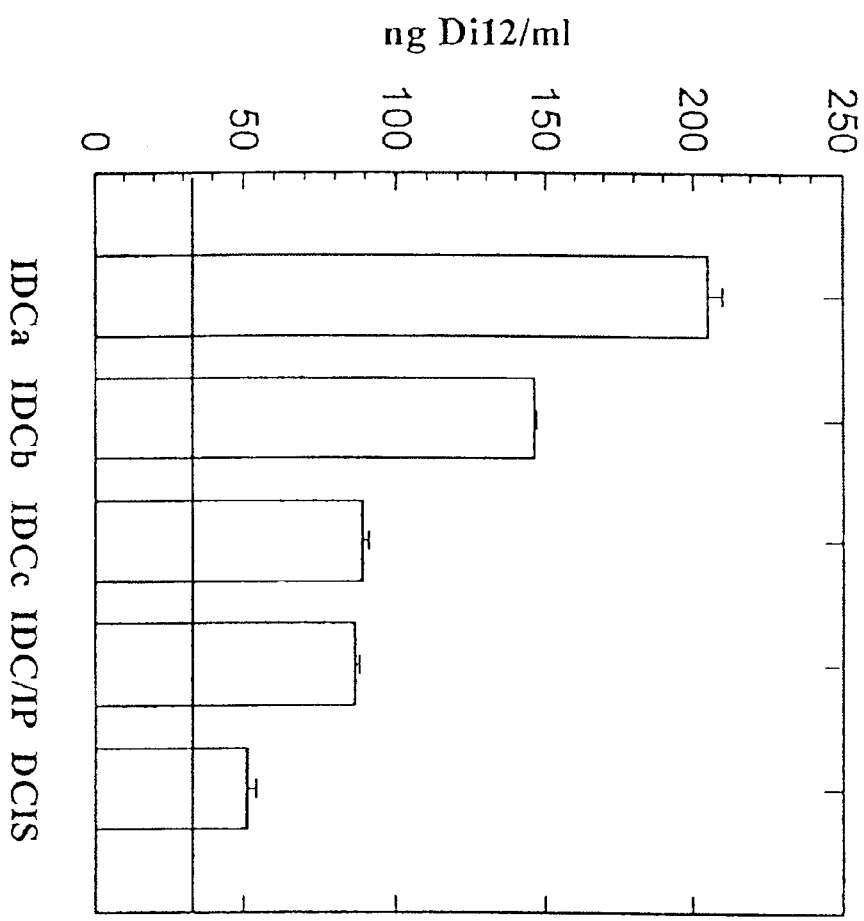

FIG. 6. Di12 gene product in breast cancer patient sera, data are representative samples of individuals graded and classified as indicated (n=3, +/− S.E). IDC accompanied by distant metastases, grade III, stage IV, IDCa. IDC with metastases, 3 of 16 axillary lymph nodes involved, grade III, stage III, IDCb. IDC no metastasis, grade I, stage I, IDCc. IDC with lntraductal papilloma, no metastasis, IDC/IP. Ductal carcinoma in situ, DCIS. Line indicates cut-off levels for Di12 positive considered samples.

5. DETAILED DESCRIPTION OF THE INVENTION

The present invention relates to the discovery and characterization of a nucleic acid molecule encoding a Di12 protein whose expression is elevated in breast cancer tissue and cell lines.

In the development of breast neoplasia, there are a subset of genes that will be specifically expressed at various stages, and a certain number of these will be critical for the progression of malignancy, especially those associated with the metastatic spread of the disease. In order to identify and isolate genes whose expression is associated with breast carcinomas in various stages of neoplastic devolvement, subtractive-hybridization cloning and differential display-PCR (Schweinfest et al., 1990, *Gene Anal Techn*, 7:64–70; Liang et al., 1992, *Science*, 257:967–971; Salesiotis et al., 1995, *Cancer Letters*, 91:47–54; Burger et al., 1996, *International Journal of Oncology*, 8:395–400) were employed. RNA was prepared from cell lines derived from a tumor and adjacent normal tissue of the same human patient. cDNAs from the normal breast cell line was subtracted from cDNAs of the breast carcinoma cell line. Over 950 clones were obtained by subtractive cloning and twenty-four clones by differential display PCR. In all, 105 cDNAs were sequenced and analyzed by computer searching and 30 were found to be unique. One of these novel cDNAS, designated herein as Di12, which may be associated with breast malignancy was selected for detailed characterization. A full length Di12 cDNA clone was isolated and antibodies were generated to study its distribution in breast cancer patient sera and tumor samples. Once identified, these differentially expressed genes will be useful for diagnosis and for monitoring disease progression, as well as for facilitating the molecular definition of specific stages of tumor development. This information will also assist in patient prognosis as well as in the selection of treatment modalities. In addition, molecular definition of new genes involved in breast tumors will yield novel targets for gene therapy and for therapeutic intervention.

The compositions of the Invention described in the following sections are recombinant mammalian Di12 DNA molecules, cloned genes, or degenerate variants thereof. Also described herein are nucleic acid probes useful for the identification of Di12 gene mutations and the use of such nucleic acid probes in diagnosing breast cancer. The compositions of the present invention further include Di12 gene products (e.g., peptides, proteins) that are encoded by the Di12 gene. The present invention also provides antibodies against Di12 gene products, or conserved variants or fragments thereof. Such antibodies can be used to measure the level of Di12 gene products in biological fluids and tissues of a patient. Thus, the present invention also encompasses methods and kits for the diagnosis, prognosis and staging of breast cancer, and the monitoring of the effect of a therapeutic treatment.

Further provided are methods for the use of the Di12 gene and/or Di12 gene products in the identification of compounds which modulate the expression of the Di12 gene. The Di12 gene is a novel gene of which the expression is upregulated in breast cancer cell lines and tissues. As such, the Di12 gene product can be involved in the mechanisms underlying the onset and development of breast cancer as well as the regional infiltration and metastatic spread of breast cancer. Thus, the present invention also provides methods for the prevention and/or treatment of breast cancer, and for the control of metastatic spread of breast cancer that is based on modulation of the expression of Di12.

5.1 THE Di12 GENE

Nucleic acid sequences of the identified Di12 gene are described herein. The full-length Di12 cDNA (1363 bp) was cloned from a CEM cDNA library. The DNA sequence contains an open reading frame of 339 amino acids. The gene sequence or amino acid sequence shows no homology to known genes or proteins. A deposit of the Di12 cDNA clone as a plasmid, pBS-Di12, in *E. coli* DH5 host was made at the American Type Culture Collection (ATCC), 10801 University Boulevard, Manassas, Va. 20110-2209 on Mar. 20, 1998, under the Accession number 209684.

As used herein, "Di12 gene" refers to (a) a gene containing the DNA sequence shown in FIG. 1B; (b) any DNA sequence that hybridizes to the complement of the DNA sequences that encode the amino acid sequence shown in FIG. 1A, under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., els., 1989, Current Protocols in Molecular Biology, Vol. I, Green Publishing Associates, Inc., and John Wiley & sons, Inc., New York, at page 2.10.3) or (c) any DNA sequence that hybridizes to the complement of the DNA sequences that encode the amino acid sequence shown in FIG. 1A, under moderately stringent conditions, e.g., washing in 0.2×SSC/0.1% SDS at 42° C. (Ausubel et al., 1989, supra), and encodes a gene product functionally equivalent to an Di12 gene product encoded by sequences shown in FIG. 1A yet which still encodes a functionally equivalent Di12 gene product.

In one embodiment of the invention, Di12 gene may also encompass fragments and degenerate variants of DNA sequences (a) through (d), including naturally occurring variants thereof. The Di12 gene fragment may be a complementary DNA (cDNA) molecule or a genomic DNA molecule that may comprise one or more intervening sequences or introns, as well as regulating regions located beyond the 5' and 3' ends of the coding region or within an intron.

A Di12 gene. sequence preferably exhibits at least about 80% overall similarity at the nucleotide level to the nucleic acid sequence depicted in FIG. 1B, more preferably exhibits at least about 85–90% overall similarity to the FIG. 1B nucleic acid sequence and most preferably exhibits at least about 95% overall similarity to the FIG. 1B nucleic acid sequence.

The Di12 gene sequences of the invention are of mammalian origin, and most preferably human.

The Di12 gene sequences of the invention further include isolated nucleic acid molecules which hybridize under highly stringent or moderate stringent conditions to at least about 6, preferably about 12, more preferably about 18, consecutive nucleotides of the Di12 gene sequences of (a)–(d).

The invention also includes nucleic acid molecules, preferably DNA molecules, that hybridize to, and are therefore the complements of, the DNA sequences (a) through (d), in the preceding paragraph. Such hybridization conditions may be highly stringent or moderately stringent, as described above. In instances wherein the nucleic acid molecules are deoxyoligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as Di12 gene antisense molecules useful, for example, in Di12 gene regulation. With respect to Di12 gene regulation, such techniques can be used to modulate, for example, the phenotype and metastatic potential of breast cancer cells. Further, such sequences may be used as part of ribozyme and/or triple helix sequences, also useful for Di12 gene regulation.

Still further, such molecules may be used as components of diagnostic methods whereby, for example, the presence of a particular Di12 allele or alternatively spliced Di12 transcript responsible for causing or predisposing one to breast cancer or other cancers may be detected.

Still further, the invention encompassing Di12 genes as a screen in an engineered yeast system, including, but not limited to, the yeast two hybrid system.

The invention also encompasses (a) DNA vectors that contain any of the foregoing Di12 coding sequences and/or their complements (e.g., antisense); (b) DNA expression vectors that contain any of the foregoing Di12 coding sequences operatively associated with a regulatory element that directs the expression of the coding sequences; and (c) genetically engineered host cells that contain any of the foregoing Di12 coding sequences operatively associated with a regulatory element that directs the expression of the coding sequences in the host cell. As used herein, regulatory elements include, but are not limited to inducible and non-inducible promoters, enhancers, operators and other elements known to those skilled in the art that drive and regulate expression. Such regulatory elements include but are not limited to the cytomegalovirus (hCMV) immediate early promoter, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

The invention includes fragments of any of the DNA sequences disclosed herein.

In addition to the Di12 gene sequences described above, homologs of such sequences, exhibiting extensive homology to the Di12 gene product present in other species can be identified and readily isolated, without undue experimentation, by molecular biological techniques well known in the art. Further, there can exist homolog genes at other genetic loci within the genome that encode proteins which have extensive homology to the Di12 gene product. These genes can also be identified via similar techniques. Still further, there can exist alternatively spliced variants of the Di12 gene.

As an example,.in order to clone a mammalian Di12 gene homolog or variants using isolated human Di12 gene sequences as disclosed herein, such human Di12 gene sequences are labeled and used to screen a cDNA library constructed from mRNA obtained from appropriate cells or tissues (e.g., breast epithelial cells) derived from the organism of interest. With respect to the cloning of such a mammalian Di12 homolog, a mammalian breast cancer cell cDNA library may, for example, be used for screening.

The hybridization and wash conditions used should be of a low stringency when the cDNA library is derived from a different type of organism than the one from which the labeled sequence was derived. Low stringency conditions are well known to those of skill in the art, and will vary predictably depending on the specific organisms from which the library and the labeled sequences are derived. For guidance regarding such conditions see, for example, gambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

With respect to the cloning of a mammalian Di12 homolog, using human Di12 sequences, for example, various stringency conditions which promote DNA hybridization can be used. For example, hybridization in 6×SSC at about 45° C., followed by washing in 2×SSC at 50° C. may be used. Alternatively, the salt concentration in the wash step can range from low stringency of about 5×SSC at 50° C., to moderate stringency of about 2×SSC at 50° C., to high stringency of about 0.2×SSC at 50° C. In addition, the temperature of the wash step can be increased from low stringency conditions at room temperature, to moderately stringent conditions at about 42° C., to high stringency conditions at about 65° C. Other conditions include, but are not limited to, hybridizing at 68° C. in 0.5M $NaHPO_4$ (pH7.2)/1 mM EDTA/7% SDS, or hybridization in 50% formamide/0.25M $NaHPO_4$ (pH 7.2)/0.25 M NaCl/1 M EDTA/7% SDS; followed by washing in 40 mM $NaHPO_4$ (pH 7.2)/1 mM EDTA/5% SDS at 50° C. or in 40 mM $NaRPO_4$ (pH7.2) 1 mM EDTA/1% SDS at 50° C. Both temperature and salt may be varied, or alternatively, one or the other variable may remain constant while the other is changed.

Alternatively, the labeled fragment may be used to screen a genomic library derived from the organism of interest, again, using appropriately stringent conditions well known to those of skill in the art.

Further, a Di12 gene homolog may be isolated from nucleic acid of the organism of interest by performing PCR using two degenerate oligonucleotide primer pools designed on the basis of amino acid sequences within the Di12 gene product disclosed herein. The template for the reaction may be cDNA obtained by reverse transcription of mRNA prepared from, for example, mammalian cell lines or tissue known or suspected to express a Di12 gene homology or allele.

The PCR product may be subcloned and sequenced to ensure that the amplified sequences represent the sequences of a Di12 gene nucleic acid sequence. The PCR fragment may then be used to isolate a full length cDNA clone by a variety of methods. For example, the amplified fragment may be labeled and used to screen a cDNA library, such as a bacteriophage cDNA library. Alternatively, the labeled fragment may be used to isolate genomic clones via the screening of a genomic library.

PCR technology may be utilized to isolate full length cDNA sequences. For example, RNA may be isolated, following standard procedures, from an appropriate cellular or tissue source (e.g., one known, or suspected, to express the Di12 gene, such as, for example, breast cancer cell lines). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of PCR technology and cloning strategies which may be used, see erg, PCR Primer, 1995, Dieffenbach et al., ed., Cold Spring Harbor Laboratory Press; Sambrook et al., 1989, supra.

Di12 gene sequences may additionally be used to isolate Di12 gene alleles and mutant Di12 gene alleles. Such mutant alleles may be isolated from individuals either known or susceptible to or predisposed to have genotype which contributes to the development of breast cancer, including metastasis. Mutant alleles and mutant allele products may then be utilized in the screening, therapeutic and diagnostic methods and systems described herein. Additionally, such Di12 gene sequences can be used to detect Di12 gene regulatory (e.g., promoter) defects which can affect the development and outcome of breast cancer.

A cDNA of a mutant Di12 gene may be isolated, for example, by using PCR, a technique which is well known to those of skill in the art. In this case, the first cDNA strand may be synthesized by hybridizing an oligo-dT oligonucleotide to mRNA isolated from tissue known or suspected to be expressed in an individual putatively carrying the mutant Di12 allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant Di12 allele to that of the normal Di12 allele, the mutation(s) responsible for the loss or alteration of function of the mutant Di12 gene product can be ascertained.

Alternatively, a genomic library can be constructed using DNA obtained from an individual suspected of or known to carry the mutant Di12 allele, or a cDNA library can be constructed using RNA from a tissue known, or suspected, to express the mutant Di12 allele. The normal Di12 gene or any suitable fragment thereof may then be labeled and used as a probe to identify the corresponding mutant Di12 allele in such libraries. Clones containing the mutant Di12 gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant Di12 allele. In this manner, gene products made from the mutant allele may be expressed and screened using standard antibody screening techniques in conjunction with antibodies raised against the normal Di12 gene product, as described, below, in Section 5.3. (For screening techniques, see, for example, Harlow, E. and Lane, eds., 1988, "Antibodies: A Laboratory Manual", Cold Spring Harbor Press, Cold Spring Harbor.) In caera where a Di12 mutation resulting in an expressed gene product with altered function (e.g., as a result of a missense or a frameshift mutation), a set of polyclonal antibodies to Di12 gene product are likely to cross-react with the mutant Di12 gene product. Library clones detected via their reaction with such labeled antibodies can be purified and subjected to sequence analysis according to methods well known to those of skill in the art.

5.2 PROTEIN PRODUCTS OF THE Di12 GENE

In another embodiment, the present invention provides Di12 gene products, or peptide fragments thereof which can be used for the generation of antibodies, in diagnostic assays, or for the identification of other cellular gene products involved in the development of cancer, such as, for example, breast cancer.

The amino acid sequence depicted in FIG. 1A represents a Di12 gene product. The Di12 gene product, sometimes referred to herein as a "Di12 protein", may additionally include those gene products encoded by the Di12 gene sequences described in Section 5.1, above.

The Di12 gene product comprises 339 amino acids. Using the Genetics Computing Group UW MOTIFS program we found: four consensus (N-X-S/T) N-glycosylation sites at positions 62, 65, 196, 277; six Ck-2 sites (consensus S/T-X-X-D/E) at positions 67, 137, 163, 189, 199, and 235; seven protein kinase C (PKC) sites (consensus S-X-K) at positions 7, 10, 100, 124, 165, 189, and 248; and various myristoylation sites. The PEPPLOT program predicts several hydrophobic regions in the Di12 protein, including a hydrophobic tail at the C-terminus. To confirm the open reading frame, the Di12 cDNA was used in an in vitro coupled transcription-translation system. As expected, a 35 kD protein was produced which is recognized by anti-Di12 antibodies in immunoprecipitation assays.

In addition, Di12 gene products may include proteins that represent functionally equivalent gene products. Such an equivalent Di12 gene product may contain deletions, additions or substitutions of amino acid residues within the amino acid sequence encoded by the Di12 gene sequences described, above, in Section 5.1, but which result in a silent change, thus producing a functionally equivalent Di12 gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

"Functionally equivalent", au utilized herein, refers to a protein capable of exhibiting a substantially similar in vivo activity as the endogenous Di12 gene products encoded by the Di12 gene sequences described in Section 5.1, above. The in vivo activity of the Di12 gene product, as used herein, refers to its association of preneoplastic and neoplastic transformation of a cell when present in an appropriate cell type, such as may, for example, occur in the onset and progression and metastasis of breast cancer.

A Di12 gene product sequence preferably exhibits at least about 80% overall similarity at the amino acid level to the amino acid sequence depicted in FIG. 1A, more preferably exhibits at least about 90% overall similarity to the FIG. 1A amino acid sequence and most preferably exhibits at least about 95% overall similarity to the FIG. 1A amino acid sequence.

Di12 gene products can also include fusion proteins comprising a Di12 gene product sequence as described in this section operatively associated to a heterologous, e.g., peptide, component. Heterologous components can include, but are not limited to sequences which facilitate isolation and purification of fusion protein, such as a matrix binding domain, or label components. Such isolation and label components are well known to those of skill in the art.

The Di12 gene products or peptid fragments thereof, or fusion proteins can be used in any assay that detects or measures Di12 gene products or in the calibration and standardization of such assay.

The Di12 gene products or peptide fragments thereof, may be produced by recombinant DNA technology using techniques well known in the art. Thus, methods for preparing the Di12 gene polypeptides and peptides of the invention by expressing nucleic acid containing Di12 gene sequences are described herein. Methods which are well known to those skilled in the art can be used to construct expression vectors containing Di12 gene product coding sequences and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA capable of encoding Di12 gene product sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the Di12 gene coding sequences of the invention. Such host-expression systems represent vehicles by which the coding sequences of interest may be produced and subsequently purified, but also represent cells which may, when transformed or transfected with the appropriate nucleotide coding sequences, exhibit the Di12 gene product of the invention in situ. These include but are not limited to microorganisms such as bacteria (e.g., *E. coli, B. subtilis*) transformed with recombinant bacteriophage DNA, plasmid DNA or cosmid DNA expression vectors containing Di12 gene product coding sequences; yeast (e.g., Saccharomyces, Pichia) transformed with recombinant yeast expression vectors containing the Di12 gene product coding sequences; insect cell systems infected with recombinant virus expression vectors (e.g., baculovirus) containing the Di12 gene product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing Di12 gene product coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the Di12 gene product being expressed. For example, when a large quantity of such a protein is to be produced, for the generation of pharmaceutical. compositions of Di12 protein or for raising antibodies to Di12 protein, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the Di12 gene product coding sequence may be ligated individually into the vector in frame with the lac Z coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The GEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiderda* cells. The Di12 gene coding sequence may be cloned individually into non-essential regions (for example the polyhedrin gene) of the virus and placed under control of an AcNPV promoter (for example the polyhedrin promoter). Successful insertion of Di12 gene coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the Di12 gene coding sequence of interest may be ligated to an adenovirus transcription/translation control complex, e.g, the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing Di12 gene product in infected hosts. (e.g., See Logan & Shenk, 1984, Proc. Natl. Acad. Sci. USA 81:3655–3659). Specific initiation signals may also be required for efficient translation of inserted Di12 gene product coding sequences. These signals include the ATC initiation codon and adjacent sequences. In cases where an entire Di12 gene, including its own initiation codon and adjacent sequences, is inserted into the appropriate expression vector, no additional translational control signals may be needed. However, in cases where only a portion of the Di12 gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, and in particular, breast cancer cell lines such as, for example, BT483, Hs578T, HTB26, BT20 and T47D, and normal mammary gland cell line such as, for example, CRL7030 and Hs578Bst.

For long-term, high-yield production of recombinant proteins, stable expression is preferred. For example, cell lines which stably express the Di12 gene product may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the Di12 gene product. Such engineered cell lines may be particularly useful in screening and evaluation of compounds that affect the endogenous activity of the Di12 gene product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026) and adenine phosphoribosyltransferase (Lowy, et al., 1980, Cell 22:817) genes can be employed in tk, hgprt or aprt cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88: 8972–8976). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with recombinant vaccinia virus are loaded onto $Ni^{2+}$ nitriloacetic acid-agarose columns and histidine-tagged proteins are selectively eluted with imidazole-containing buffers.

The Di12 gene products can also be expressed in transgenic animals. Animals of any species, including, but not limited to, mice, rats, rabbits, guinea pigs, sheep, pigs, micro-pigs, goats, and non-human primates, e.g., baboons, monkeys, and chimpanzees may be used to generate Di12 transgenic animals.

Any technique known in the art may be used to introduce the Di12 gene transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the Di12 transgene in all their cells, as well as animals which carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, M. et al., 1992, Proc. Natl. Acad. Sci, USA 89; 6232–6236).

The regulatory sequences required for such a cell-type specific activation will depend upon the particular cell type of interest, and will be apparent to those of skill in the art. When it is desired that the Di12 gene transgene be integrated into the chromosomal site of the endogenous Di12 gene, gene targeting is preferred. Briefly, when such a technique is to be utilized, vectors containing some nucleotide sequences homologous to the endogenous Di12 gene are designed for the purpose of integrating, via homologous recombination with chromosomal sequences, into and disrupting the function of the nucleotide sequence of the endogenous Di12 gene. The transgene may also be selectively introduced into a particular cell type, thus inactivating the endogenous Di12 gene in only that cell type, by following, for example, the teaching of Gu et al. (Gu, et al., 1994, Science 265: 103–106). The regulatory sequences required for such a cell-type specific inactivation will depend upon the particular cell type of interest, and will be apparent to those of skill in the art.

Methods for the production of single-copy transgenic animals with chosen sites of integration are also well known to those of skill in the art. See, for example, Bronson et al. (Brongon, S. K. et al., 1996, Proc. Natl. Acal. Sci. USA 93:9067–9072), which is incorporated herein by reference in its entirety.

Once transgenic animals have been generated, the expression of the recombinant Di12 gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of Di12 gene-expressing tissue, may also be evaluated immunocytochemically using antibodies specific for the Di12 transgene product.

5.3 ANTIBODIES TO Di12 GENE PRODUCTS

In another embodiment, the present invention encompasses antibodies or fragments thereof capable of specifically recognizing one or more Di12 gene product epitopes or epitopes of conserved variants or peptide fragments of the Di12 gene products. Such antibodies may include, but are not limited to, polyclonal antibodies, monoclonal antibodies (mAbs), humanized or chimeric antibodies, single chain antibodies, Fab fragments, F(ab')$_2$ fragments, Fv fragments, fragments produced by a Fab expression library, anti-idiotypic (anti-Id) antibodies, and epitope-binding fragments of any of the above.

Such antibodies may be used, for example, in the detection of a Di12 gene product in an biological sample and may, therefore, be utilized as part of a diagnostic or prognostic technique whereby patients may be tested for abnormal levels of Di12 gene products, and/or for the presence of abnormal forms of the such gene products. Such antibodies may also be included as a reagent in a kit for use in a diagnostic or prognostic technique. Such antibodies may also be utilized in conjunction with, for example, compound screening schemes, as described, below, in Section 5.4.2, for the evaluation of the effect of test compounds on Di12 gene product levels and/or activity. Additionally, such antibodies can be used in conjunction with the gene therapy techniques described, below, in Section 5.4.3, to, for example, evaluate the normal and/or engineered Di12-expressing cells prior to their introduction into the patient.

Antibodies to anti-Di12 gene product may additionally be used in a method for the inhibition of abnormal Di12 gene product activity. Thus, such antibodies may, therefore, be utilized as part of cancer treatment methods.

Described herein are methods for the production of antibodies of such antibodies or fragments thereof. Any of such antibodies or fragments thereof may be produced standard immunological methods or by recombinant expression of nucleic acid molecules encoding the antibody or fragments thereof in an appropriate host organism.

For the production of antibodies against a Di12 gene product, various host animals may be immunized by injection with a Di12 gene product, or a portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as a Di12 gene product, or an antigenic functional derivative thereof. For the production of polyclonal antibodies, host animals such as those described above, may be immunized by injection with Di12 gene product supplemented with adjuvants as also described above.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al.9 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, 1988, Science 242 421–426;Huston et al., 1988, Proc. Natl. Acad. Sci. USA 85:5879–5883; and Ward et al., 1989, Nature 334:544–546) can be adapted to produce single chain antibodies against Di12 gene products. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., 1988, Science 242:1038–1041).

Antibody fragments which recognize specific epitopes may be generated by known techniques. For example, such fragments include but are not limited to: the $F(ab')_2$ fragments which can be produced by pepsin digestion of the antibody molecule and the Pab fragments which can be generated by reducing the disulfide bridges of the $F(ab')_2$ fragments. Alternatively, Fab expression libraries may be constructed (Huse et al., 1989, Science, 246:1275–1281) to allow rapid and easy identification of monoclonal Fab fragments with the desired specificity.

5.4 USES OF THE Di12 GENE, GENE PRODUCTS, AND ANTIBODIES

In various embodiments, the present invention provides various uses of the Di12 gene, the Di12 gene product including peptide fragments thereof, and of antibodies directed against the Di12 gene product and peptide fragments thereof. Such uses include, for example, prognostic and diagnostic evaluation of cancer, and the identification of subjects with a predisposition to a cancer, :as described, below.

In one embodiment, the present invention provides a variety of methods for the diagnostic and prognostic evaluation of breast cancer. Such methods may, for example, utilize reagents such as the Di12 gene nucleotide sequences described in Sections 5.1, and antibodies directed against Di12 gene products, including peptide fragments thereof, as described, above, in Section 5.2. Specifically, such reagents may be used, for example, for: (1) the detection of the presence of Di12 gene mutations, or the detection of either over- or under-expression of Di12 gene nRNA preneoplastic or neoplastic relative to normal cells or the qualitative or quantitative detection of other alleic forms of Di12 transcripts which may correlate with breast cancer or susceptibility toward neoplastic changes, and (2) the detection of an over-abundance of Di12 gene product relative to the non-disease state or the presence of a modified (e.g., less than full length) Di12 gene product which correlates with a neoplastic state or a progression toward neoplasia or metastasis.

The methods described herein may be performed, for example, by utilizing pre-packaged diagnostic test kits comprising at least one specific Di12 gene nucleic acid or anti-Di12 gene antibody reagent described herein, which may be conveniently used, e.g., in clinical settings or in home settings, to diagnose patients exhibiting preneopiastic or neoplastic abnormalities, and to screen and identify those individuals exhibiting a predisposition to such neoplastic changes.

Nucleic acid-based detection techniques are described, below, in Section 5.4.1. Peptide detection techniques are described, below, in Section 5.4.2.

5.4.1 DETECTION OF Di12 GENE NUCLEIC ACID MOLECULES

Mutations or polymorphisms within the Di12 gene can be detected by utilizing a number of techniques. Nucleic acid from any nucleated cell can be used as the starting point for such assay techniques, and may be isolated according to standard nucleic acid preparation procedures which are well known to those of skill in the art. For the detection of Di12 mutations, any nucleated cell can be used as a starting source for genomic nucleic acid. For the detection of Di12 transcripts or Di12 gene products, any cell type or tissue in which the Di12 gene is expressed, such as, for example, breast cancer cells, including metastases, may be utilized.

Genomic DNA may be used in hybridization or amplification assays of biological samples to detect abnormalities involving Di12 gene structure, including point mutations, insertions, deletions and chromosomal rearrangements. Such assays may include, but are not limited to, direct sequencing (Wong, C. et al., 1987, Nature 330:384–386), single stranded conformational polymorphism analyses (SSCP; Orita, M. et al., 1989, Proc. Natl. Acad. Sci. USA 86:2766–2770), heteroduplex analysis (Keen, T. J. et al., 1991, Genomics 11:199–205; Perry, D. J. & Carrell, R. W., 1992), denaturing gradient gel electrophoresis (DGGE;. Myers, R. M. et al., 1985, Nucl. Acids Res. 13:3131–3145), chemical mismatch cleavage (Cotton, R. G. et al., 1988, Proc. Natl. Acad. Sci. USA 85:4397–4401) and oligonucleotide hybridization (Wallace, R. B. et al., 1981, Nucl. Acids Res. 9:879–894; Lipshutz, R. J. et al., 1995, Biotechniques 19:442–447).

Diagnostic methods for the detection of Di12 gene specific nucleic acid molecules, in patient samples or other appropriate cell sources, may involve the amplification of specific gene sequences, e.g., by the polymerase chain reaction (PCR; see Mullis, K. B., 1987, U.S. Pat. No. 4,683,202), followed by the analysis of the amplified molecules using techniques well known to those of skill in the art, such as, for example, those listed above. Utilizing analysis techniques such as these, the amplified sequences can be compared to those which would be expected if the nucleic acid being amplified contained only normal copies of the Di12 gene in order to determine whether a Di12 gene mutation exists.

Further, well-known genotyping techniques can be performed to type polymorphisms that are in close proximity to mutations in the Di12 gene itself. These polymorphisms can be used to identify individuals in families likely to carry mutations. If a polymorphism exhibits linkage disequilibrium with mutations in the Di12 gene, it can also be used to identify individuals in the general population likely to carry mutations. Polymorphisms that can be used in this way include restriction fragment length polymorphisms (RFLPs), which involve sequence variations in restriction enzyme target sequences, single-base polymorphisms and simple sequence repeat polymorphisms (SSLPs).

For example, Weber (U.S. Pat. No. 5,075,217, which is incorporated herein by reference in its entirety) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers which are so closely spaced exhibit a high frequency co-inheritance, and are extremely useful in the identification of genetic mutations, such as, for example, mutations within the Di12 gene, and the diagnosis of diseases and disorders related to Di12 mutations.

Also, Caskey et al. (U.S. Pat. No. 5,364,759, which is incorporated herein by reference in its entirety) describe a DNA profiling assay for detecting short tri and tetra nucleotide repeat sequences. The process includes extracting the DNA of interest, such as the Di12 gene, amplifying the extracted DNA, and labelling the repeat sequences to form a genotypic map of the individual's DNA.

A Di12 probe could additionally be used to directly identify RFLPs. Additionally, a Di12 probe or primers derived from the Di12 sequence could be used to isolate genomic clones such as YACs, BACs, PACs, cosmids, phage or plasmids. The DNA contained in these clones can be screened for single-base polymorphisms or simple sequence length polymorphisms (SSLPs) using standard hybridization or sequencing procedures.

Alternative diagnostic methods for the detection of Di12 gene-specific mutations or polymorphisms can include hybridization techniques which involve for example, contacting and incubating nucleic acids including recombinant DNA molecules, cloned genes or degenerate variants thereof, obtained from a sample, e.g., derived from a patient sample or other appropriate cellular source, with one or more labeled nucleic acid reagents including recombinant DNA molecules, cloned genes or degenerate variants thereof, as described in Section 5.1, under conditions favorable for the specific annealing of these reagents to their complementary sequences within the Di12 gene. Preferably, the lengths of these nucleic acid reagents are at least 15 to 30 nucleotides. After incubation, all non-annealed nucleic acids are removed from the nucleic acid:Di12 molecule hybrid. The presence of nucleic acids which have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described in Section 5.1 are easily removed. Detection of the remaining, annealed, labeled Di12 nucleic acid reagents is accomplished using standard techniques well-known to those in the art. The Di12 gene sequences to which the nucleic acid reagents have annealed can be compared to the annealing pattern expected from a normal Di12 gene sequence in order to determine whether a Di12 gene mutation is present.

Quantitative and qualitative aspects of Di12 gene expression can also be assayed. For example, RNA from a cell type or tissue known, or suspected, to express the Di12 gene, such as breast cancer cells, including metastases, may be isolated and tested utilizing hybridization or PCR techniques as described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the Di12 gene. Such analyses may reveal both quantitative and qualitative aspects of the expression pattern of the Di12 gene, including activation or inactivation of Di12 gene expression and presence of alternatively spliced Di12 transcripts.

In one embodiment of such a detection scheme, a cDNA molecule is synthesized from an RNA molecule of interest by reverse transcription. All or part of the resulting cDNA is then used as the template for a nucleic acid amplification reaction, such as a PCR or the like. The nucleic acid reagents used as synthesis initiation reagents (ed., primers) in the reverse transcription and nucleic acid amplification steps of this method are chosen from among the Di12 gene nucleic acid reagents described in Section 5.1. The preferred lengths of such nucleic acid reagents are at least 9–30 nucleotides.

For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Such RT-PCR techniques can be utilized to detect differences in Di12 transcript size which may be due to normal or abnormal alternative splicing. Additionally, such techniques can be performed using standard techniques to detect quantitative differences between levels of full length and/or alternatively spliced Di12 transcripts detected in normal individuals relative to those individuals having cancer or exhibiting a predisposition toward neoplastic changes.

In the case where detection of specific alternatively spliced species is desired, appropriate primers and/or hybridization probes can be used, such that, in the absence of such sequence, no amplification would occur. Alternatively, primer pairs may be chosen utilizing the sequence data depicted in FIG. 1D to choose primers which will yield fragments of differing size depending on whether a particular exon is present or absent from the transcript Di12 transcript being utilized.

As an alternative to amplification techniques, standard Northern analyses can be performed if a sufficient quantity of the appropriate cells can be obtained. Utilizing such techniques, quantitative as well as size related differences between Di12 transcripts can also be detected.

Additionally, it is possible to perform such Di12 gene expression assays "in situ", i.e., directly upon tissue sections (fixed and/or frozen) of patient tissue obtained from biopsies or resections, such that no nucleic acid purification is necessary. Nucleic acid reagents such as those described in Section 5.1 may be used as probes and/or primers for such in situ procedures (see, for example, Nuovo, G. J., 1992, "IPCR In Situ Hybridization: Protocols And Applications", Raven Press, NY).

5.4.2 DETECTION OF Di12 GENE PRODUCTS

Antibodies directed against wild type or mutant Di12 gene products or conserved variants or peptide fragments thereof, which are discussed, above, in Section 5.2, may also be used as diagnostics and prognostics, as described herein. Such diagnostic methods, may be used to detect abnormalities in the level of Di12 gene expression, or abnormalities in the structure and/or temporal, tissue, cellular, or subcellular location of Di12 gene product. Antibodies, or fragments of antibodies, such as those described below, may be used to screen potentially therapeutic compounds in vitro to determine their effects on Di12 gene expression and Di12 peptide production. The compounds which have beneficial effects on breast cancer can be identified and a therapeutically effective dose determined.

The tissue or cell type to be analyzed will generally include those which are known, or suspected, to express the Di12 gene, such as, for example, breast cancer cells or metastatic cells. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety. The isolated cells can be derived from cell culture or from a patient. The analysis of cell taken from culture may be a necessary step to test the effect of compounds on the expression of the Di12 gene.

Preferred diagnostic methods for the detection of Di12 gene products or conserved variants or peptide fragments thereof, may involve, for example, immunoassays wherein the Di12 gene products or conserved variants, including gene products which are the result of alternatively spliced transcripts, or peptide fragments are detected by their interaction with an anti-Di12 gene product-specific antibody.

For example, antibodies, or fragments of antibodies, such as those described, above, in Section 5.3, useful in the present invention may be used to quantitatively or qualitatively detect the presence of Di12 gene products or conserved variants or peptide fragments thereof. The antibodies (or fragments thereof) useful in the present invention may, additionally, be employed histologically, as in immunofluorescence or immunoelectron microscopy, for in situ detection of Di12 gene products or conserved variants or peptide fragments thereof. In situ detection may be accomplished by removing a histological specimen from a patient, such as paraffin embedded sections of breast tissues and applying thereto a labeled antibody of the present invention. The antibody (or fragment) is preferably applied by overlaying the labeled antibody (or fragment) onto a biological sample. Since the Di12 gene product is present in the cytoplasm, it may be desirable to introduce the antibody inside the cell, for example, by making the cell membrane permeable. Through the use of such a procedure, it is possible to determine not only the presence of the Di12 gene product, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays for Di12 gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of identifying Di12 gene products or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled Di12 gene specific antibody. The solid phase support may then be washed with the buffer a second time to remove unbound antibody. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod, Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-Di12 gene product antibody may be determined according to well known methods. Those skilled in the art will be able to determine operative and optimal assay conditions for each determination by employing routine experimentation.

One of the ways in which the Di12 gene peptide-specific antibody can be detectably labeled is by linking the same to an enzyme and use in an enzyme immunoassay (EIA) (Voller, A, "The Enzyme Linked Immunosorbent Assay (ELISA)", 1978, Diagnostic Horizons 2:1–7, Microbiological Associates Quarterly Publication, Walkersville, Md.); Voller, A. et al., 1978, J. Clin. Pathol. 31:507–520; Butler, J. E., 1981, Meth. Enzymol. 73:482–523; Maggio, E. (ed.), 1980, Enzyme Immunoassay, CRC Press, Boca Raton, Fla.,; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible. to detect Di12 gene peptides through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In various embodiments, the present invention provides the measurement of Di12 gene products, and the uses of such measurements in clinical applications.

As used herein, the term "soluble" shall mean those molecules that are "spontaneously released"; i.e., released by normal or pathologic physiological processes of a cell.

The measurement of Di12 gene product of the invention can be valuable in detecting and/or staging breast cancer in a subject, in screening of breast cancer in a population, in differential diagnosis of the physiological condition of a subject, and in monitoring the effect of a therapeutic treatment on a subject.

The present invention also provides for the detecting, diagnosing, or staging of breast cancer, or the monitoring of treatment of breast cancer by measuring in addition to Di12 gene product at least one other marker, such as receptors or differentiation antigens. For example, serum markers selected from, for example but not limited to, carcinoembryonic antigen (CEA), CA15-3, CA549, CAM26, M29, CA27.29 and MCA can be measured in combination with Di12 gene product to detect, diagnose, stage, or monitor treatment of breast cancer. In another embodiment, the prognostic indicator is the observed change in different marker levels relative to one another, rather than the absolute levels of the markers present at any one time. These measurements can also aid in predicting therapeutic outcome and in evaluating and monitoring the overall disease status of a subject.

In a specific embodiment of the invention, soluble Di12 gene product alone or in combination with other markers can be measured in any body fluid of the subject including but not limited to blood, serum, plasma, milk, urine, saliva, pleural effusions, synovial fluid, spinal fluid, tissue infiltrations and tumor infiltrates. The measurement of. soluble Di12 gene products in blood or serum is preferred with respect to the development of a test kit which is to be used in clinics and homes.

Any of numerous immunoassays can be used in the practice of the instant invention, ouch as those described in Section 5.4.2. Antibodies, or antibody fragments containing the binding domain, which can be employed include but are not limited to suitable antibodies among those in Section 5.3 and other antibodies known in the art or which can be obtained by procedures standard in the art such as those described in Section 5.3.

5.4.3 DETECTING AND STAGING A BREAST CANCER IN A SUBJECT

In one embodiment of the present invention, measurement of Di12 gene product or fragment thereof, or soluble Di12 gene product can be used to detect breast cancer in a subject or to stage the breast cancer in a subject.

Staging refers to the grouping of patients according to the extent of their disease. Staging is useful in choosing treatment for individual patients, estimating prognosis, and comparing the results of different treatment programs. Staging of breast cancer is performed initially on a clinical basis, according to the physical examination and laboratory radiologic evaluation. The most widely used clinical staging system is the one adopted by the International Union against Cancer (UICC) and the American Joint Committee on Cancer (AJCC) Staging and End Results Reporting. It is based on the tumor-nodes-metastases (TNM) system as detailed in the 1988 Manual for *Staging of Cancer*. Breast cancer diseases or conditions which may be detected and/or staged in a subject according to the present invention include but are not limited to those listed in Table I.

TABLE I

| STAGING OF BREAST CANCER | |
|---|---|
| T | PRIMARY TUMORS |
| TX | Primary tumor cannot be assessed |
| T0 | No evidence of primary tumor |
| Tis | Carcinoma in situ: intraductal carcinoma, lobular carcinoma, or Paget's disease with no tumor |

TABLE I-continued

STAGING OF BREAST CANCER

| | |
|---|---|
| T1 | Tumor 2 cm or less in its greatest dimension |
| | a. 05 cm or less in greatest dimension |
| | b. Larger than 0.5 cm, but not larger than 1 cm in greatest dimension |
| | c. Larger than 1 cm, but not larger than 2 cm in greatest dimension |
| T2 | Tumor more than 2 cm but not more than 5 cm in greatest dimension |
| T3 | Tumor more than 5 cm in its greatest dimension |
| T4 | Tumor of any size with direct extension to chest wall or to skin. Chest wall includes ribs, intercostal muscles, and serratus anterior muscle, but not pectoral muscle. |
| | a. Extension to chest wall |
| | b. Edema (including peau d'orange), ulceration of the skin of the breast, or satellite skin nodules confined to the same breast |
| | c. Both of the above |
| | d. Inflammatory carcinoma |
| Dimpling of the skin, nipple retraction, or any other skin changes except those in T4b may occur in T1, T2 or T3 without affecting the classification. | |
| N | REGIONAL LYMPH NODES |
| NX | Regional lymph nodes cannot be assessed (e.g., previously removed) |
| N0 | No regional lymph node metastases |
| N1 | Metastasis to movable ipsilateral axillary node(s) |
| N2 | Metastases to ipsilateral axillary nodes fixed to one another or to other structures |
| N3 | Metastases to ipsilateral internal mammary lymph node(s) |
| M | DISTANT METASTASIS |
| M0 | No evidence of distant metastasis |
| M1 | Distant metastases (including metastases to ipsilateral supraclavicular lymph nodes) |

Any immunoassay, such as those described in Section 5.4.2 can be used to measure the amount of Di12 gene product or soluble Di12 gene product which is compared to a baseline level. This baseline level can be the amount which is established to be normally present in the tissue or body fluid of subjects with various degrees of the disease or disorder. An amount present in the tissue or body fluid of the subject which is similar to a standard amount, established to be normally present in the tissue or body fluid of the subject during a specific stage of breast cancer, is indicative of the stage of the disease in the subject. The baseline level could also be the level present in the subject prior to the onset of disease or the amount present during remission of the disease.

In specific embodiments of this aspect of the invention measurements of levels of the Di12 gene product or soluble Di12 gene product can be used in the detection of infiltrative ductal carcinoma (IDC) or the presence of metastases or both. Progressively higher levels of Di12 gene products or soluble Di12 gene product are associated with IDC, and more aggressive forms of the disease, such as IDC with regional lymph node involvement, and IDC with distant metastases.

In another embodiment of the invention, the measurement of soluble Di12 gene product, fragments thereof or immunologically related molecules can be used to differentially diagnose in a subject a particular disease phenotype or physiological condition as distinct as from among two or more phenotypes or physiological conditions. For example, measurements of Di12 gene product or soluble Di12 gene product levels may be used in the differential diagnosis of infiltrative ductal carcinoma, as distinguished from ductal carcinoma in situ or benign fibroadenomas. To this end, for example, the measured amount of the soluble Di12 gene product is compared with the amount of the soluble molecule normally present in body fluid of a subject with one of the suspected physiological conditions. A measured amount of the soluble molecule similar to the amount normally present in a subject with one of the physiological conditions, and not normally present in a subject with one or more of the other physiological conditions, is indicative of the physiological condition of the subject.

5.4.4 MONITORING THE EFFECT OF A THERAPEUTIC TREATMENT

The present invention provides a method for monitoring the effect of a therapeutic treatment on a subject who has undergone the therapeutic treatment.

Clinicians very much need a procedure that can be used to monitor the efficacy of these treatments. Soluble Di12 gene product can be identified and detected in breast cancer patients with different manifestations of disease, providing a sensitive assay to monitor therapy. The therapeutic treatments which may be evaluated according to the present invention include but are not limited to radiotherapy, surgery, chemotherapy, vaccine administration, endocrine therapy, immunotherapy, and gene therapy, etc. The chemotherapeutic regimens include, but are not limited to administration of drugs such as, for example, methotrexate, fluorouracil, cyclophosphamide, doxorubicin, and taxol. The endocrine therapeutic regimens include, but are not limited to administration of tamoxifen, progestins, etc.

The method of the invention comprises measuring at suitable time intervals before, during, or after therapy, the amount of a Di12 gene product or soluble Di12 gene product, or both. Any change or absence of change in the amount of the Di12 gene product or soluble Di12 gene product or in the amount of the total Di12 gene product can be identified and correlated with the effect of the treatment on the subject.

In particular, the serum levels of soluble Di12 gene product bears a direct relationship with severity of breast cancer and poor prognosis. Since serum soluble Di12 gene product levels are generally undetectable or negligible in normal individuals, generally, a decrease in the level of detectable soluble Di12 gene product after a therapeutic treatment is associated with efficacious treatment.

In a preferred aspect, the approach that can be taken is to determine the levels of soluble Di12 gene product levels at different time points and to compare these values with a baseline level. The baseline level can be either the level of the marker present in normal, disease free individuals; and/or the levels present prior to treatment, or during remission of disease, or during periods of stability. These levels can then be correlated with the disease course or treatment outcome.

5.5 SCREENING ASSAYS FOR COMPOUNDS THAT MODULATE Di12 ACTIVITY

The present invention further provides methods for the identification of compounds that may, through its interaction with the Di12 gene or Di12 gene product, affect the onset, progression and metastatic spread of breast cancer.

The following assays are designed to identify: (i) compounds that bind to Di12 gene products; (ii) compounds that bind to other intracellular proteins that interact with a Di12 gene product; (iii) compounds that interfere with the interaction of the Di12 gene product with other intracellular proteins; and (iv) compounds that modulate the activity of Di12 gene (i.e., modulate the level of Di12 gene expression and/or modulate the level of Di12 gene product activity).

Assays may additionally be utilized which identify compounds which bind to Di12 gene regulatory sequences (e.g., promoter sequences). See e.g., Platt, K. A., 1994, J. Biol. Chem. 269:28558–28562, which is incorporated herein by reference in its entirety, which may modulate the level of Di12 gene expression.

Such intracellular proteins may be involved in the onset, development and metastatic spread of breast cancer.

Compounds identified via assays such as those described herein may be useful, for example, in elaborating the biological function of the Di12 gene product, and for ameliorating symptoms of breast cancer., Assays for testing the effectiveness of compounds, identified by, for example, techniques such as those described in Section 5.5.1, are discussed, below, in Section 5.5.3. It is to be noted that the compositions of the invention include pharmaceutical compositions comprising one or more of the compounds identified via such methods. Such pharmaceutical compositions can be formulated, for example, as discussed, below, in Section 5.7.

5.5.1 IN VITRO SCREENING ASSAYS FOR COMPOUNDS THAT BIND TO THE D12 GENE PRODUCT

In vitro systems may be designed to identify compounds capable of interacting with, e.g., binding to, the Di12 gene products of the invention. Compounds identified may be useful, for example, in modulating the activity of wild type and/or mutant Di12 gene products, may be useful in elaborating the biological function of the Di12 gene product, may be utilized in screens for identifying compounds that disrupt normal Di12 gene product interactions, or may in themselves disrupt such interactions.

The principle of the assays used to identify compounds that interact with the Di12 gene product involves preparing a reaction mixture of the Di12 gene product and the test compound under conditions and for a time sufficient to allow the two components to interact with, e.g., bind to, thus forming a complex, which can represent a transient complex, which can be removed and/or detected in the reaction mixture. These assays can be conducted in a variety of ways. For example, one method to conduct such an assay would involve anchoring Di12 gene product or the test substance onto a solid phase and detecting Di12 gene product/test compound complexes anchored on the solid phase at the end of the reaction. In one embodiment of such a method, the Di12 gene product may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is completes unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for Di12 gene product or the test compound to anchor any complexes formed in solution, and a labeled antibody specific for the other component of the possible complex to detect anchored complexes.

5.5.2 ASSAYS FOR INTRACELLULAR PROTEINS THAT INTERACT WITH THE Di12 GENE PRODUCT

Any method suitable for detecting protein-protein interactions may be employed for identifying Di12 protein-intracellular protein interactions.

Among the traditional methods which may be employed are co-immunoprecipitation, crosslinking and co-purification through gradients or chromatographic columns. Utilizing procedures such as these allows for the isolation of intracellular proteins which interact with Di12 gene products. Once isolated, such an intracellular protein can be identified and can, in turn, be used, in conjunction with standard techniques, to identify additional proteins with which it interacts. For example, at least a portion of the amino acid sequence of the intracellular protein which interacts with the Di12 gene product can be ascertained using techniques well known to those of skill in the art, such as via the Edman degradation technique (see, e Creighton, 1983, "Proteins: Structures and Molecular Principles", W.H. Freeman & Co., N.Y., pp.34–49). The amino acid sequence obtained may be used as a guide for the generation of oligonucleotide mixtures that can be used to screen for gene sequences encoding such intracellular proteins. screening may be accomplished, for example, by standard hybridization or PCR techniques. Techniques for the generation of oligonucleotide mixtures and the screening are well-known. (See, e.g., Ausubel, supra., and PCR Protocols: A Guide to Methods and Applications, 1990, Innis, M. et al., eds. Academic Press, Inc., New York).

Additionally, methods may be employed which result in the simultaneous identification of genes which encode the intracellular protein interacting with the Di12 protein. These methods include, for example, probing expression libraries with labeled Di12 protein, using Di12 protein in a manner similar to the well known technique of antibody probing of $\lambda$gt11 libraries.

One method which detects protein interactions in vivo, the two-hybrid system, can be used. One version of this system has been described (Chien et al., 1991, Proc. Natl. Acad. Sci. USA, 88:9578–9582) and is commercially available from Clontech (Palo Alto, Calif.).

5.5.3 ASSAYS FOR COMPOUNDS THAT INTERFERE WITH Di12 GENE PRODUCT/INTRACELLULAR MACROMOLECULAR INTERACTION

The Di12 gene products of the invention may, in vivo, interact with one or more intracellular macromolecules, such as proteins. Such macromolecules may include, but are not limited to, nucleic acid molecules and those proteins identified via methods such as those described, above, in Section 5.5.2. For purposes of this discussion, such intracellular macromolecules are referred to herein as "interacting partners". Compounds that disrupt Di12 interactions in this way may be useful in regulating the activity of the Di12 gene product, including mutant Di12 gene products. Such compounds may include, but are not limited to molecules such as peptides, and the like, as described, for example, in Section 5.5.1. above, which would be capable of gaining access to the intracellular Di12 gene product.

The basic principle of the assay systems used to identify compounds that interfere with the interaction between the Di12 gene product and its intracellular interacting partner or partners involves preparing a reaction mixture containing the Di12 gene product, and the interacting partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of Di12 gene product and its intracellular interacting partner. Control reaction mixtures are incubated without the test compound or with a placebo. The formation of any complexes between the Di12 gene protein and the intracellular interacting partner is then detected. The formation of a complex in the control reaction, but not in the reaction mixture containing the test compound, indicates that the compound interferes with the interaction of the Di12 gene protein and the interacting partner. Additionally, complex formation within reaction mixtures containing the test compound and normal Di12 gene protein may also be compared to complex formation within reaction mixtures containing the test compound and a mutant Di12 gene protein. This comparison may be important in those cases wherein it is desirable to identify compounds that disrupt interactions of mutant but not normal Di12 gene proteins.

The assay for compounds that interfere with the interaction of the Di12 gene products and interacting partners can be conducted in a heterogeneous or homogeneous format. Heterogeneous assays involve anchoring either the Di12 gene product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the Di12 gene products and the interacting partners, e.g., by competition, can be identified by conducting the reaction in the presence of the test substance; i.e., by adding the test substance to the reaction mixture prior to or simultaneously with the Di12 gene protein and intracellular interacting partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the Di12 gene product or the interacting partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the Di12 gene product or interacting partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt pre-formed complexes can be detected.

Alternatively, the reaction can be conducted in a liquid phase in the presence or absence of the test compound, the reaction products separated from unreacted components, and complexes detected; e., using an immobilized antibody specific for one of the interacting components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the Di12 gene protein and the interacting partner is prepared in which either the Di12 gene product or its interacting partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt Di12 gene protein/intracellular interacting partner interaction can be identified.

In a particular embodiment, the Di12 gene product can be prepared for immobilization using recombinant DNA techniques described in Section 5.1, above. For example, the Di12 coding region can be fused to a glutathione-S-transferase (GST) gene using a fusion vector, such as pGEX-5X-1, in such manner that its interacting activity is maintained in the resulting fusion protein. The intracellular interacting partner can be purified and used to raise a monoclonal antibody, using methods routinely practiced in the art and described above, in Section 5.2. This antibody can be labeled with the radioactive isotope $^{125}I$, for example, by methods routinely practiced in the art. In a heterogeneous assay, e.g., the GST-Di12 fusion protein can be anchored to glutathione-agarose beads. The intracellular interacting partner can then be added in the presence or absence of the test compound in a manner that allows interaction, e.g., binding, to occur. At the end of the reaction period, unbound material can be washed away, and the labeled monoclonal antibody can be added to the system and allowed to bind to the complexed components. The interaction between the Di12 gene protein and the intracellular interacting partner can be detected by measuring the amount of radioactivity that remains associated with the glutathione-agarose beads. A successful inhibition of the interaction by the test compound will result in a decrease in measured radioactivity.

Alternatively, the GST-Di12 gene fusion protein and the intracellular interacting partner can be mixed together in liquid in the absence of the solid glutathione-agarose beads.

The test compound can be added either during or after the species are allowed to interact. This mixture can then be added to the glutathione-agarose beads and unbound material is washed away. Again the extent of inhibition of the Di12 gene product/interacting partner interaction can be detected by adding the labeled antibody and measuring the radioactivity associated with the beads.

5.5.4 CELL-BASED ASSAYS FOR IDENTIFICATION OF COMPOUNDS WHICH MODULATE Di12 ACTIVITY

Cell-based methods are presented herein which identify compounds capable of treating breast cancer by modulating Di12 activity. Specifically, such assays identify compounds which affect Di12-dependent processes, such as but not limited to changes in cell morphology, cell division, differentiation, adhesion, motility, or phosphorylation, dephosphorylation of cellular proteins. Compounds identified via such methods can, for example, be utilized in methods for treating breast cancer and metastasis.

In one embodiment, the cell-based assays are based on expression Qf the Di12 gene product in a mammalian cell and measuring the Di12-dependent process. Any mammalian cells that can express the Di12 gene and allow the functioning of the Di12 gene product can be used, in particular, cancer cells derived from the breast, such as BT483, Hs578T, HTB26, BT20 and T47D. Normal mammary gland cell lines such as, for example, CRL7030 and Hs578Bst, may also be used provided that a Di12 gene product is produced. Recombinant expression of the Di12 gene in these cells can be achieved by methods described in Section 5.2. In these assays, cells producing functional Di12 gene products are exposed to a test compound for an interval sufficient for the compound to modulate the activity of the Di12 gene product. The activity of Di12 gene product can be measured directly or indirectly through the dectetion or measurement of Di12-dependent cellular processes. As a control, a cell not producing the Di12 gene product may be used for comparisons. Depending on the cellular process, any techniques known in the art may be applied to detect or measure it.

5.6 METHODS FOR TREATMENT OF BREAST CANCER

Described below are methods and compositions for treating breast cancer using the Di12 gene or gene product as a therapeutic target. The outcome of a treatment is to at least produce in a treated subject a healthful benefit, which in the case of breast cancer, includes but is not limited to remission of the cancer, palliation of the symptoms of the cancer, control of metastatic spread of the cancer.

All such methods comprise methods which modulate Di12 gene activity and/or expression which in turn modulate the phenotype of the treated cell.

As discussed, above, successful treatment of breast cancer can be brought about by techniques which serve to decrease Di12 activity. Activity can be decreased by, for example, directly decreasing Di12 gene product activity and/or by decreasing the level of Di12 gene expression.

For example, compounds such as those identified through assays described, above, in Section 5.5, above, which decrease Di12 activity can be used in accordance with the invention to treat breast cancer. As discussed in Section 5.5, above, such molecules can includes but are not limited to peptides, including soluble peptides, and small organic or inorganic molecules, and can be referred to as Di12 antagonists. Techniques for the determination of effective doses and administration of such compounds are described, below, in Section 5.7.

Further, antisense and ribozyme molecules which inhibit Di12 gene expression can also be used in accordance with the invention to reduce the level of Di12 gene expression, thus effectively reducing-the level of Di12 gene product present, thereby decreasing the level of Di12 activity. Still further, triple helix molecules can be utilized in reducing the level of Di12 gene activity. Such molecules can be designed to reduce or inhibit either wild type, or if appropriate, mutant target gene activity. Techniques for the production and use of such molecules are well known to those of skill in the art.

Any technique which serves to selectively administer nucleic acid molecules to a cell population of interest can be used, for example, by using a delivery complex. Such a delivery complex can comprise an appropriate nucleic acid molecule and a targeting means. Such targeting means can comprise, for example, sterols, lipids, viruses or target cell specific binding agents. Viral vectors that can be used with recombiant viruses include, but are not limited to adenovirus, adeno-associated virus, herpes'simplex virus, vaccinia virus, and retrovirus vectors, in addition to other particles that introduce DNA into cells, such as liposomes.

5.6.1 ANTISENSE MOLECULES

The use of antisense molecules as inhibitors of gene expression is a specific, genetically based therapeutic approach (for a review, see Stein, in. Ch. 69, Section 5 "Cancer: Principle and Practice of Oncology", 4th ed., ed. by DeVita et al., J.B. Lippincott, Philadelphia 1993). The present invention provides the therapeutic or prophylactic use of nucleic acids of at least six nucleotides that are antisense to a gene or cDNA encoding, Di12 or a portion thereof. An "antisense" Di12 nucleic acid as used herein refers to a nucleic acid capable of hybridizing to a portion of a Di12 RNA (preferably mRNA) by virtue of some sequence complementarity. The invention further provides pharmaceutical compositions comprising an effective amount of the Di12 antisense nucleic acids of the invention in a pharmaceutically acceptable carrier, as described infra.

In another embodiment, the invention is directed to methods for inhibiting the expression of a Di12 nucleic acid sequence in a mammalian cell in vitro or in vivo comprising providing the cell with an effective amount of a composition comprising an Di12 antisense nucleic acid of the invention.

The antisense nucleic acid of the invention may be complementary to a coding and/or noncoding region of a Di12 mRNA. The antisense molecules will bind to the complementary Di12 gene mRNA transcripts and reduce or prevent translation. Absolute complementarity, although preferred, is not required. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Nucleic acid molecules that are complementary to the 5' end of the message, e.g., the 5' untranslated sequence up to and including the AUG initiation codon, should work most efficiently at inhibiting translation. However, sequences complementary to the 3' untranslated sequences of mRNAs have recently shown to be effective at inhibiting translation of mRNAs as well. See generally, Wagner, R., 1994, Nature 372:333–335. Thus, oligonucleotides complementary to either the 5'- or 3'-non- translated, non-coding regions of the Di12 gene, as shown, for example, in FIG. 1, could De used in an antisense approach to inhibit translation of endogenous Di12 gene mRNA.

Nucleic acid molecules complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-,3'- or coding region of target or pathway gene mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad, Sci. 84;648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-tromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanirne, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenino, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide, An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphogphonate oligonucleotides can be prepared by use of controlled pore glass polymer supports (Sarin et al., 1988, Proc. Natl. Acad. Sci. U.S.A. 85:7448–7451), etc.

While antisense nucleotides complementary to the Di12 coding region could be used, those complementary to the transcribed untranslated region are most preferred. For example, antisense oligonucleotides having the following sequence can be utilized in accordance with the invention:
a) 5'-CATGGCTACCATAGCTT-3' which is complementary to nucleotides −14 to +3 in FIG. 1B (SEQ ID NO: 3)
b) 5'-CATGGCTACCATAGCTTTCGCAGC-3' which is complementary to nucleotides −21 to +3 in FIG. 1B (SEQ ID NO: 4).
c) 5'-CATGGCTACCATAGCTTTCGCAGCAGCACCA-3' which is complementary to nucleotides −28 to +3 in FIG. 1B (SEQ ID NO: 5).
d) 5-CATGCOTACCATAGCTTTCGCAGCAGCACCA-GCTTk-3' which is complementary to nucleotides −35 to +3 in FIG. 1B (SEQ ID NO: 6).
e) 51-AGCCATGGCTACCATAGCTTTCGCAGCAGC-ACCA-3' which is complementary to nucleotides −28 to +6 in FIG. 1B (SEQ ID NO: 7).
f) 5'-GGCTACCATAGCTTTCGCAGCAGCACCAGCG-CTTA-3' which is complementary to nucleotides −35 to −1 in FIG. 1B (SEQ ID NO: 8).
g) 5'-TTTCGCAGCAGCACCA-3' which is complementary to nucleotides −28 to −13 in FIG. 1B (SEQ ID NO: 9).

The antisense molecules should be delivered to cells which express the Di12 gene in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous Di12 gene transcripts and thereby prevent translation of the Di12 gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art, and described in Section 5.6.4. Vectors can be plasmid, viral, or others known in the art, used for replication and expression in mammalian cells. Expression of the sequence encoding the antisense RNA can be. by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296;39–42),:etc. Any type of plasmid, cosmid, YAC or viral vector can be used to prepare the recombinant DNA construct which can be introduced directly into the tissue site. Alternatively, viral vectors can be used which selectively infect the desired tissue.

5.6.2 RIBOZYME MOLECULES

Ribozymes are enzymatic RNA molecules capable of catalyzing the specific cleavage of RNA (For a review see, for example Rossi, J., 1994, Current Biology 4:469–471). The mechanism of ribozyme action involves sequence specific hybridization of the ribozyme molecule to complementary target RNA, followed by a endonucleolytic cleavage. The composition of ribozyme molecules must include one or more sequences complementary to the target gene mRNA, and must include the well known catalytic sequence responsible for mRNA cleavage. For this sequence, see U.S. Pat. No. 5,093,246, which is incorporated by reference herein in its entirety. As such, within the scope of the invention are engineered hammerhead motif ribozyme molecules that specifically and efficiently catalyze endonucleolytic cleavage of RNA sequences encoding target gene proteins.

Ribozyme molecules designed to catalytically cleave Di12 gene mRNA transcripts can also be used to prevent translation of Di12 gene mRNA and expression of target or pathway gene. (See, e.g., PCT International Publication WO90/11164, published Oct. 4, 1990; Sarver et al., 1990, Science 247:1222–1225). While ribozymes that cleave mRNA at site specific recognition sequences can be used to destroy Di12 gene mRNAs, the use of hammerhead ribozymes is preferred. Hammerhead ribozymes cleave mRNAs at locations dictated by flanking regions that form complementary bane pairs with the target mRNA. The sole requirement is that the target mRNA have the following sequence of two bases: 5'-UG-3'. The construction and production of hammerhead ribozymesis well known in the art and is described more fully in Haseloff and Gerlach, 1988, Nature, 334;585–791. Preferably the ribozyme is engineered so that the cleavage recognition site is located near the 5' end of the Di12 gene. mRNA; i.e., to increase efficiency and minimize the intracellular accumulation of non-functional mRNA transcripts.

For example, hammerhead ribozymes having the following sequences can be utilized in accordance with the invention:

a) 5'-CAUCAAAGCNGNNNNNNCNGAGNAGUCGG-CUAC-3' which will cleave human Di12 mRNA between nucleotides −1 and +1 in FIG. 1B SEQ ID NO: 10).

b) 5'-ACCCAAAGCNGNNNNNNCNGAGNAGUCU-UUGTJ-3' which will cleave human Di12 mRNA between nucleotides −54 and 55 in FIG. 1B (SEQ ID NO: 11).

c) 5'-UCGCAAAGCNGNNNNNNCNGAGNAGUCC-AGCAC-3' which will cleave human Di12 mRNA between nucleotides −20 and −21 in FIG. 1B (SEQ ID NO: 12).

d) 5'-UACCAAAGCNGNNNNNNCNGAGNAGUCA-GCUUU-3' which will cleave human Di12 mRNA between nucleotides −9 and −10 in FIG. 1B (SEQ ID NO: 13).

The ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO 88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in an Di12 gene.

As in the antisense approach, the ribozymes can be composed of modified oligonucleotides (e.g. for improved stability, targeting, etc.) and should be delivered to cells which express the Di12 gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous Di12 gene messages and inhibit translation. Because ribozymes unlike antisense molecules, are catalytic, a lower intracellular concentration is required for efficiency.

Anti-sense RNA and DNA, ribozyme, and triple helix molecules of the invention can be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules can be generated by in vitro and in vivo transcription of DNA sequences encoding the antisense RNA molecule. Such DNA sequences can be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules can be introduced as a means of increasing intracellular stability and half-life. Possible modifications include, but genare not limited to, the addition of flanking sequences of ribo- or deoxy- nucleotides to the 5' and/or 3' ends of the molecule or the use of phosphorothioate or 2' O-methyl rather than phosphodiesterase linkages within the oligodeoxyribonucleotide backbone.

5.6.3 THERAPEUTIC ANTIBODIES

Antibodies exhibiting capability to downregulate Di12 gene product activity can be utilized to treat breast cancer. Such antibodies can be generated using standard techniques described in section 5.3, above, against full length wild. type or mutant Di12 proteins, or against peptides corresponding to portions of the proteins. The antibodies include but are not limited to polyclonal, monoclonal, Fab fragments, single chain antibodies, chimeric antibodies, and the like.

Because Di12 is an intracellular protein, it is preferred that internalizing antibodies be used. However, lipofectin or liposomes can be used to deliver the antibody or a fragment of the Fab region which binds to the Di12 gene product epitope into cells. Where fragments of the antibody are used, the smallest inhibitory fragment which binds to the Di12 protein's binding domain is preferred. For example, peptizes having an amino acid sequence corresponding to the domain of the variable region of the antibody that binds to the Di12 protein can be used. Such peptides can be synthesized chemically or produced via recombinant DNA technology using methods well known in the art (e.g., see Creighton, 1983, supra; and Sambrook et al., 1989, above). Alternatively, single chain antibodies, such as neutralizing antibodies, which bind to intracellular epitopes can also be administered. Such single chain antibodies can be administered, for example, by expressing nucleotide sequences encoding single-chain antibodies within the target cell population by utilizing, for example, techniques such as those described in Marasco et al. (Marasco, W. et al., 1993, Proc. Natl. Acad. Sci. USA 90:7889–7893).

5.6.4 GENE THERAPY

Gene therapy refers to treatment or prevention of cancer performed by the administration of a nucleic acid to a subject who has cancer or in whom prevention or inhibition of cancer is desirable. In this embodiment of the invention, the therapeutic nucleic acid produces intracellularly an antisense nucleic acid molecules that mediates a therapeutic effect by inhibiting Di12 expression. In another embodiment, nucleic acids comprising a sequence encoding a dominant negative mutant Di12 protein or non-functional fragment or derivative thereof, are administered to inhibit Di12 function by interfereing with the interactions of Di12 and with other molecules in the cell.

For general reviews of the methods of gene therapy, see Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIBTECH 11(5) :155–215). Methods commonly known in the art of recombinant DNA technology which can be used are described in Ausubel et al. (eds.), 1993,Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds.), 1994, Current Protocols in Human Genetics, John Wiley & Sons, NY.

In one aspect, the therapeutic nucleic acid comprises a Di12 nucleic acid that is part of an expression vector that expresses a dominant non-functional Di12 protein or fragment or chimeric protein thereof in cancer cells. The function of Di12 is thought to be mediated by protein-protein interactions. Therefore, Di12 mutants that are defective in function but effective in binding to its interacting partner can be used as a dominant negative mutant to compete with the wild type Di12. Dominant non-functional Di12 can be engineered for expression in cancer cells that inappropriately overexpress Di12.

In a preferred aspect, the therapeutic nucleic acid comprises an antisense Di12 nucleic acid that is part of an expression vector that produces the antisense molecule in a suitable host. In particular, such a nucleic acid has a promoter operably linked to the antisense Di12 sequence, said promoter being inducible or constitutive, and, optionally, tissue-specific.

In another particular embodiment, a nucleic acid molecule is used in which the antisense Di12 sequences and any other desired sequences are flanked by regions that promote homologous recombination at a desired site in the genome, thus providing for intrachromosomal expression of the antisense Di12 nucleic acid (Koller and Smithies, 1989, Proc. Natl. Acad. Sci. USA 86:8932–8935; Zijlstra et al., 1989, Nature 342:435–438).

Delivery of the nucleic acid into a patient may be either direct, in which case the patient is directly exposed to the nucleic acid or nucleic acid-carrying vector or a delivery complex, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the antisense nucleic acid molecule or encoded non-functional Di12 gene product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in biopolymers (e.g., poly-$\beta$-1->4-N-acetylglucosamine polysaccharide; see U.S. Pat. No. 5,635, 493), encapsulation in liposomes, microparticles, or microcapsules, or by administering it in linkage to a peptide which is known to enter the nucleus, by administering it in linkage to a ligand Subject to receptor-mediated endocytosis (see e.g., Wu and Wu, 1987, J. Biol. Chem. 262:4429–4432), etc. In another embodiment, a nucleic acid-ligand complex can be formed in which the ligand comprises a fusogenic viral peptide to disrupt endosomes, allowing the nucleic acid to avoid lysogomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al,); WO 92/22635 dated Dec. 23, 1992 (Wilson et al.); WO92/20316 dated Nov. 26, 1992 (Findeis etal.); WO93/14188 dated Jul. 22, 1993 (Clarke et al.), WO 9/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342:435–438).

In a specific embodiment, a viral vector that contains the antisense Di12 nucleic acid is used. For example, a retroviral vector can be used (see Miller et al., 1993, Meth. Enzymol. 217:581–599). These retroviral vectors have been modified to delete retroviral sequences that are not necessary for packaging of the viral genome and integration into host cell DNA. The antisense Di12 nucleic acid to be used in gene therapy is cloned into the vector, which facilitates delivery of the gene into a patient. More detail about retroviral vectors can be found in Boesen et al., 1994, Biotherapy 6:291–302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644–651; Kiem et al., 1994, Blood 83:1467–1473; Salmons and Gunzberg, 1993, Human Gene Therapy 4:129–141; and Grossman and Wilson, 1993, Curr. opin. in Genetics and Devel. 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499–503 present a review of adenovirus-based gene therapy. Bout et al., 1994, Human Gene Therapy 5.3–10 demonstrated the use of adenovirus vectors to transfer genes to the respiratory epithelia of rhesus monkeys. Other instances of the use of adenoviruses in gene therapy can be found in Rosenfeld et al., 1991, Science 252:431–434; Rosenfeld et al., 1992, Cell 68:143–155; and Mastrangeli et al., 1993, J. Clin. Invest. 91:225–234. Adeno-associated virus (AAV) has also been proposed for use in gene therapy (Walsh et al. 1993, Proc. Soc. Exp. Biol. Med. 204:289–300).

The form and amount of therapeutic nucleic acid envisioned for use depends on the severity of the cancer, desired effect, patient state, etc., and can be determined by one skilled in the art.

Endogenous Di12 gene expression can also be reduced by inactivating or "knocking out" the gene or its promoter using targeted homologous recombination. (E.g., see Smithies et al., 1985, Nature 317:230–234; Thomas & Capecchi, 1987, Cell 51:503–512; Thompson et al., 1989 Cell 5:313–321; each of which is incorporated by reference herein in its entirety).

For example, a mutant, non-functional Di12 gene (or a completely unrelated DNA sequence) flanked by DNA homologous to the endogenous Di12 gene (either the coding regions or regulatory regions of the Di12 gene) can be used, with or without a selectable marker and/or a negative selectable marker, to transfect cells that express Di12 gene in vivo. Insertion of the DNA construct, via targeted homologous recombination, results in inactivation of the Di12 gene. Such approaches are particularly suited where modifications to ES (embryonic stem) cells can be used to generate animal offspring with an inactive Di12 gene (eg., see Thomas & Capecchi 1987 and Thompson 1989, supra). Such techniques can also be utilized to generate animal models of breast cancer. It should be noted that this approach can be adapted for use in humans provided the recombinant DNA constructs are directly administered or targeted to the required site in vivo using appropriate viral vectors, e.g., herpes virus vectors.

Alternatively, endogenous Di12 gene expression can be reduced by targeting deoxyribonucleotide sequences complementary to the regulatory region of the Di12 gene (i.e., the Di12 gene promoter and/or enhancers) to form triple helical structures that prevent transcription of the Di12 gene in target cells in the body. (see generally, Helene, C. 1991, Anticancer Drug Des., 6(6):569–84; Helene, C., et al., 1992, Ann, N.Y. Acad. Sci., 660:27–36; and Maher, L. J., 1992, Bioassays 14(12):807–15).

5.7 PHARMACEUTICAL PREPARATIONS AND METHODS OF ADMINISTRATION

The compounds and nucleic acid sequences described herein can be administered to a patient at therapeutically effective doses to treat breast cancer. A therapeutically effective dose refers to that amount of a compound sufficient to result in a healthful benefit in the treated subject.

5.7.1 EFFECTIVE DOSE

Toxicity and therapeutic efficacy of compounds can be determined by standard pharmaceutical procedures in cell cultures or experimental animals, e.g, for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

5.7.2 FORMULATIONS AND USE

Pharmaceutical compositions for use in accordance with the present invention can be formulated in conventional manner using one or more physiologically acceptable carriers or excipients.

Thus, the compounds and their physiologically acceptable salts and solvents can be formulated for administration by inhalation or insufflation (either through the mouth or the nose) or oral, buccal, parenteral or rectal administration.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microerygtallins cellulose or calcium hydrogen phosphate); lubricants (e.g., magnesium stearate, talc or silica); disintegrants (e.g., potato starch or sodium starch glycolate); or wetting agents (eq., sodium lauryl gulphato). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (eg., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound.

For buccal administration the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator can be formulated containing a powder mix of the compound and a suitable powder base such as lactose or starch.

The compounds can be formulated for parenteral administration (i.e., intravenous or intramuscular) by injection, via, for example, bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents sucn as suspending, stabilizing and/or dispersing agents. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

6 EXAMPLE

IDENTIFICATION OF A NOVEL GENE INVOLVED IN BREAST CANCER

This example describes the isolation and characterization of the Di12 gene. Two procedures: subtractive hybridization cloning and differential display PCR, were undertaken in order to isolate genes whose expression is associated with breast cancer in various stages of neoplastic development. The Di12 gene which is overexpressed in cancer cells was selected for detailed characterization.

6.1. MATERIALS AND METHODS

Cell Lines.

The human breast cancer cell lines (Hs578T, HTB26, BT20, and T47D) and the normal breast cell lines Hs578Bst and CRL7370 were obtained from the ATCC (Rockville, Md.). The BT-483 cell line was a gift from Prof. W. J. Gullick, Hammersmith Hospital, London.

2 Tissue and Serum Samples.

Forty seven paraffin-embedded samples from breast tissues were obtained from the Pathology Department at Bradford Royal Infirmary (BRI), Ten fresh breast tissue samples for RNA isolation were provided by the Surgical. Pathology Department at Women's College Hospital. All patient samples received were graded for the presence of malignancy by a pathologist to ensure characterization. Sixty serum samples examined were randomly collected by BRI-Biochemistry laboratory from breast cancer patients of the cancer unit. Utilization of patient material and diagnostic information was approved by the respective institutional ethical review committees.

Northern Blotting and RT-PCR.

Total RNA from breast cancer cell lines or tissues was isolated using the RNAzol B method, and probed with cDNA fragments as described previously (1995, Salesiotis et al., *Cancer Letters*, 91:47–54; 1996, Burger et al., *International Journal of Oncology*, 8:395–400). The RT-PCR amplifications were performed with Di12 specific primers (sense: 5'-CGG CTG CTG GTG CTG ATT TG-3') (SEQ ID NO: 14) and (artisense: 5'-CCA CGT GTC GCG TCA CCA AT-3') (SEQ ID NO: 15) designed to generate a 415 bp product.

Subtractive Cloning.

The lambda ZAP II phagemid system (Stratagene, La Jolla Calif.) was used for the construction of directional libraries in opposite orientation using the EcoRI and XhoI sites. cDNA's were prepared from the 'normal' breast cell line Hs578Bst and the tumor cell line Hs578T as described (1990, Schweinfest et al., *Gene Anal Techn*, 7:64–70; 1995, Salesiotis et al., *Cancer Letters*, 91:47–54; 1996, Burger et al., *International Journal of Oncology*, 8:395–400).

Differential Display.

The differential display using the RNA prepared from normal (Hs578Bst) and breast cancer cell-lines (Hs578T, BT474, and BT2) using a kit from GenHunter Corp., (Brookline, Mass.)(1992, Liang et. al., *Science*, 257.:967–971). DNA from differentially displayed bands of interest were recovered, reamplified and cloned into pBS or TA cloning vectors (Stratagene or Invitrogen, San Diego, Calif., respectively) and further characterized by DNA sequence analysis and Northern blotting.

6.2. RESULTS

6.2.1. CLONING OF BREAST CANCER-ASSOCIATED GENES

Using subtractive-hybridization techniques to identify genes linked to breast cancers, cDNA libraries enriched for breast cancer-associated cDNAs were generated. Single-stranded cDNA clones derived from a normal human breast cell-line, Hs578Bst, were subtracted using single-stranded cDNA clones of a breast carcinoma cell-line, Hs578T, derived from the adjacent malignant tissue of the same patient. A total of 950 clones from the breast cancer enriched cDNA subtraction library were obtained and screened by Southern hybridization with the total cDNA from the Hs578T cDNA library. Clonog positively expressed in tumor cDNAs and negative in normal cDNAs were further analyzed by restriction mapping. The DNA sequence from eighty-one clones with inserts greater than 250 bp was determined and analyzed by FASTA and BLAST programs (GCG, LTW, Madison, Wis. and NIH, NILM, Basic Local Alignment Search Tool, respectively). These analyses found 32 cDNAs to be novel and not previously identified, (e.g., as having no significant homology to genes listed in databases GenBank, EMBL)

A second strategy for obtaining differentially expressed genes in breast cancer cells was to clone PCR amplified cDNAs reverse transcribed from RNAs derived from the normal (Hs578Bst) and tumor (Hs578T, BT474, and BT20) breast cell lines. The cDNAs differentially expressed from these human breast cell lines were cloned, and twenty-four of these were sequenced and compared to those in the databases; three of them were found to be novel genes; having a differential pattern of expression in cell-lines and tissues. Among the known cDNAs, several of them include: c-fgr, E2A, tPA, osteonectin, and insulin-like growth factor binding protein, which have been previously reported to be involved in breast and other cancers (1991, Abts et al., *Leuk. Res.*, 15:987–97; 1989, Murre et al., *Cell*, 56:777–783; 1991, Shimasaki et al., *J. Biol. Chem.*, 266:10646–10653).

6.2.2. FULL LENGTH cDNA CLONING AND PROTEIN SEQUENCE ANALYSIS OF Di12

The full-length Di12 cDNA (1363 bp) was cloned from a CEM cDNA library. The DNA sequence contains an open reading frame of 339 amino acids in which the first ATG, (G-C-C-A-T-C-G) is homologous to the Kozak consensus (A/G-X-X-A-T-G-G) (1981, Kozak, M., *Nucleic Acids Res.*, 9:5233–5262); the protein translation start site (FIG. 1B). Using the GCG UW MOTIFS program we found: four consensus (N-X-S/T) N-glycosylation sites at positions 62, 65, 196, 277; six Ck-2 sites (consensus S/T-X-X-D/E) at positions 67, 137, 163, 189, 199, and 235; seven PKC sites (consensus S-X-K) at positions 7, 10, 100, 124, 165, 189, and 248; and various myristoylation sites. The PEPPLOT program predicts several hydrophobic regions in the Di12 protein, including a hydrophobic tail at the C-terminus. To confirm the open reading frame, the Di12 cDNA was subcloned into the pSG5 expression vector and was used in an in vitro coupled transcription-translation system. As expected, a 35 kD protein was produced with the vector containing the Di12 insert (FIG. 2, Lane 1), but not with the control vector (pSG5) without the insert (data not shown). The 35 kD expressed product is also recognized by anti-Di12 antibodies in immunoprecipitation assays (FIG. 2, Lanes 3 and 4) and not by preimmune serum (FIG. 2, Lane 2).

6.2.3. EXPRESSION OF Di12 RNA

Figure 3A:
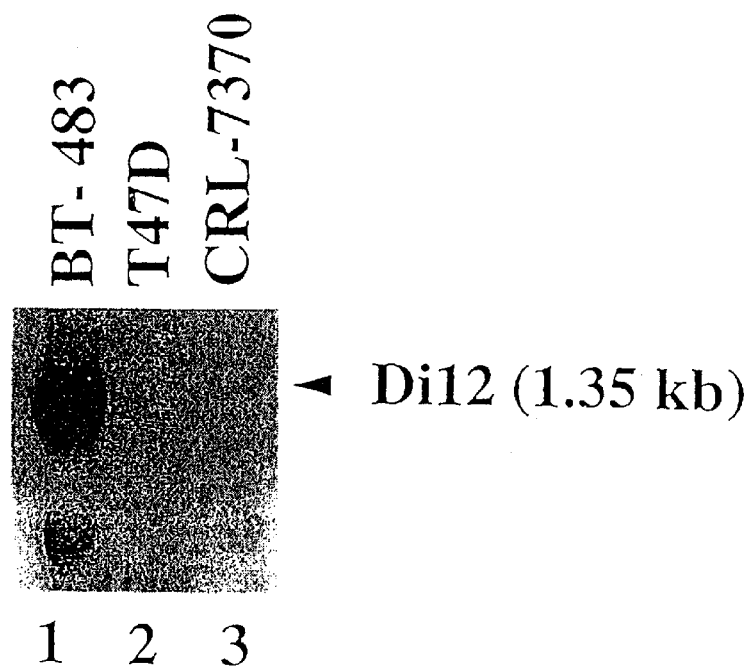

The Di12 gene was found to be expressed as a 1.35 kb RNA in several breast cancer cell lines, with the highest levels observed in BT483 (FIG. 3A, lane 1), lower levels in Hs578T (FIG. 3C, lane 2), and very weak or no expression was observed in HTB26, BT-20 and T47D cell lines (FIG. 3A and C). Di12 expression wag undetectable in the normal mammary gland cell line CRL 7370 (FIG. 3A, lane 3), and was barely detectable in another normal breast cell line Hs578Bst (e.g., only after prolonged exposures using increased amounts of poly(A) RNA (data not shown). Di12 RNA was found to be expressed in various normal human (FIG. 3E) and rat (FIG. 3F) tissues, including lung, kidney, pancreas, and heart, but it was expressed at low levels or not detectable in the brain, placenta, and liver. The similar tissue expression pattern of Di12 in rat and human tissues indicates that this gene is likely to be conserved between mammalian species and may have similar function(s) as well.

7. EXAMPLE

DIAGNOSIS AND STAGING OF BREAST CANCER

This example illustrates the association of Di12 gene expression with breast cancer, and in particular infiltrating ductal carcinomas.

7.1. MATERIALS AND METHODS

Di12 Antibodies.

Antibodies were raised in rabbits against the N-terminal 12 amino acid synthetic peptide: MARDGASIKTIK (SEQ ID NO: 16) (cf. FIG. 2).

Immunohistochemistry.

Immunohistochemical localization of Di12 protein was examined in two paraffin-embedded breast cancer cell lines and various primary tissue samples including thirty three malignant IDC, three DCIS, five LCIS and six normal breast samples from reduction mammoplasties with the HistoStain™ SP Kit (rabbie, Zymed, San Prancisco, Calif.) as described (1995, Soibeyran et al., *Breast Cancer Res. Treat.*, 34:119–128). The Elston-modified Bloom and Richardson method was used for histological grading of breast tumors (1991, Elston et al., *Histopathol.*, 19:403–410).

ELISA Assay.

Detection of Di12 gene product with Di12 antibody in patient sera was performed using the ELISA procedure from the ExtrAvidin Peroxidase Staining Kit (anti-human, Sigma, Poole, Dorset, UK). Specific binding was detected with a biotin/streptavidin-peroxidase system 2,2'-azino-bis-(3-ethylbenzthioazline-6-sulfuric acid) as substrate, the absorption (at 405 nm) of positive reactions was compared to known Di12 antibody concentrations.

7.2. RESULTS

In order to determine if Di12 is differentially expressed in different types of breast cancer or if it is stage related, we examined fresh tissue samples obtained from normal breast, fibroadenomas and fibrocystic disease with non-proliferative and proliferative changes both with or without atypia, as well as ductal carcinomas in situ and infiltrating ductal carcinomas were analyzed by immunohistochemistry, ELISA, and RTPCR.

7.2.1. IMMUNOHISTOCHEMICAL ANALYSIS

Figure 3B:
Figures 3C, 3D:
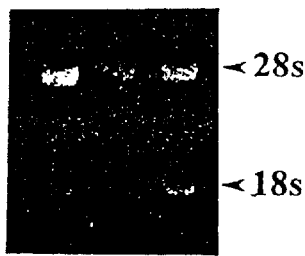
Figure 3E:
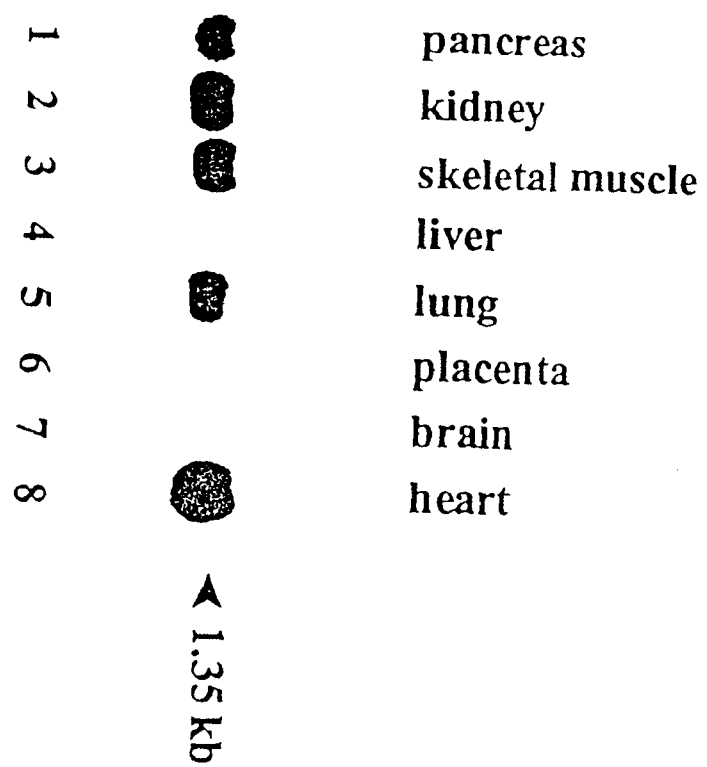
Figure 3F:
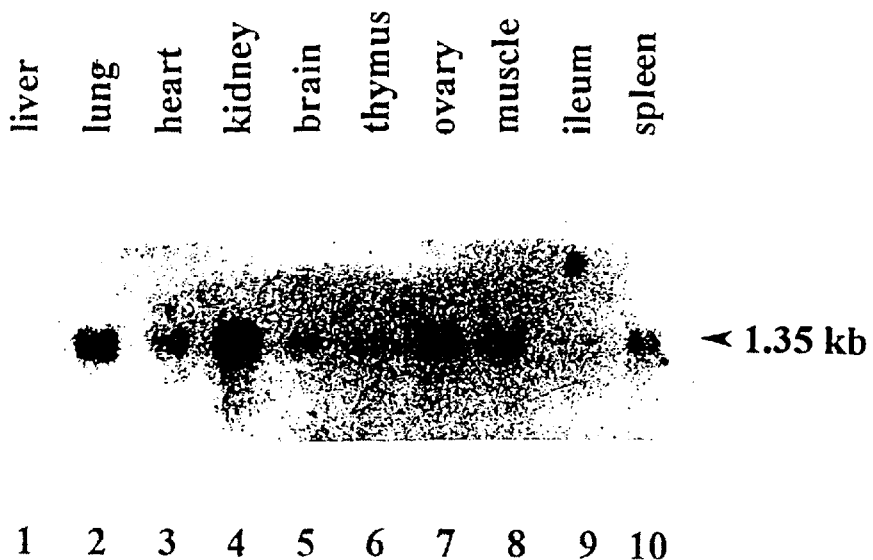
Figure 3G:
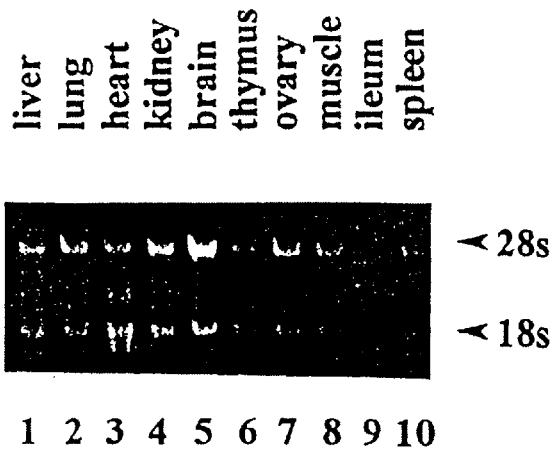

As shown above, Northern blot analysis indicated that the breast cancer cell lines BT483 and Hs578T produce high and low levels of Di12 RNA respectively (FIG. 3A–C). Paraffin embedded sections of these cells were therefore included as positive and negative controls.

Figure 4F:
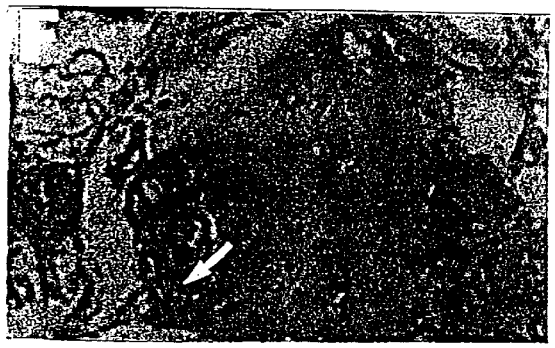
Figure 4G:
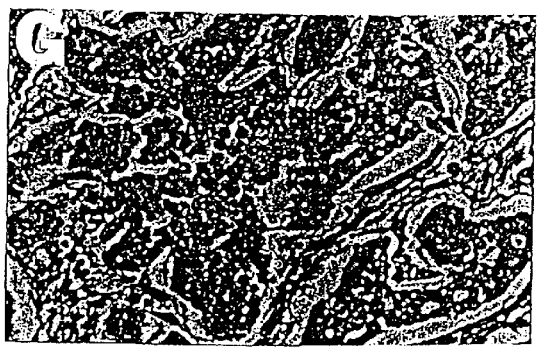
Figure 4H:
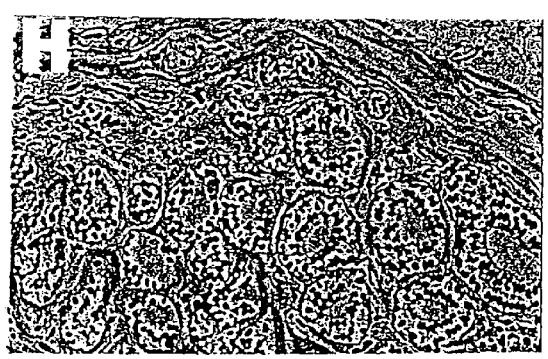

A total of forty-seven paraffin embedded normal and primary malignant breast tissues were screened for tissue distribution of Di12 gene product. In particular, six normal breast tissues from breast reductions, 5 lobular carcinomas in situ, 3 ductal carcinomas in situ and 33 IDCs of various grades and stages of disease progression were examined. A representative panel of immunostained sections from cell line and tissue samples is shown (FIGS. 4A–H). Specific, strong Di12 staining was seen in cytoplasm of IDCs with a slight increase in perinuclear regions of less well differentiated cells with poor prognosis (FIGS. 4E–G). In contrast, normal breast tissue (FIG. 4H) showed no Di12-specific staining. As expected, BT 483 cells showed the strongest Di12 protein staining (FIGS. 4A and D); whereas Hs578T, with low levels of Di12 gene expression, showed weaker staining with Di12 antibody (FIG. 4C).

7.2.2. RT-PCR ANALYSIS

In order to complement the protein expression data and confirm if Di12 is differentially expressed in different types of breast cancer or is stage related, fresh tissue samples from normal breast, fibroadenomas and fibrocystic disease with non-proliferative and proliferative changes and those with or without atypia, as well as ductal carcinomas in situ and infiltrating ductal carcinomas were analyzed by reverse transcription-polymerase chain reaction (RT-PCR). Our results show that Di12 expression is associated with more than eighty percent of the confirmed IDC specimens and was absent in non-malignant samples (FIG. 5). Interestingly, the only, Di12-negative IDC specimen was in fact described histologically as having extensive tissue necrosis with a single intraductal papilloma localized distal from the tumor site. RT-PCR, although not quantitative, did generate bands with different intensities, suggesting varying levels of Di12 gene expression between samples.

7.2.3. IMMUNOASSAY

To investigate whether Di12 gene product might be useful as a serological marker for infiltrating ductal carcinomas, sera from sixty patients were examined for the presence of Di12 gene product using specific Di12 antibody. An enzyme linked immunosorbent assay was developed to detect circulating Di12 protein. Thirty-seven out of sixty breast cancer sera examined showed elevated levels for the Di12 gene product. Background levels for ELISA-Di12 was determined as 35 ng/ml in the assays using standardized quantities of Di12 antibody coated plates. The Di12 ELISA positive samples were nearly all associated with invasive ductal carcinomas (IDC), with higher levels noted in sera from patients having lymph node or distant metastases (FIG. 6). Significantly, sera from three ovarian cancer patients, as well as all three patients with benign breast disease, were negative for Di12 product by this assay. The Di12 serum protein determined by ELISA appeared to be related to grade and stage of disease, with DCIS having the lowest levels and IDC accompanied with metastatic disease being the highest levels as depicted in FIG. 6.

7.3. DISCUSSION

The evaluation of Di12 gene expression in breast carcinomas as described in sections 7.2.1 and 7.2.2 showed that it is predominantly associated with tumors of the infiltrating ductal type, but not with ductal carcinoma in situ, benign fibroadenomas, or normal breast tissue obtained from reduction mammoplasty. Moreover the Di12 antibody data as described in 7.2.3 were in close agreement with RT-PCR and Northern blot data obtained from cell lines and primary tissues. By both Northern blot and immunohistochemistry, there were high levels of Di12 expression found in BT483 and Hs 578T breast cancer cell lines. Similarly a good correlation in Di12 gene expression by RT-PCR, was observed with the positive staining of Di12 protein by immunoperoxidase technique in primary tissues, further confirming the sensitivity and accuracy of each of the methods employed. In general homogeneous cytoplasmic distribution of Di12 specific protein was seen throughout infiltrating pleomorphic cells and malignant cells invading vascular spaces, but not in normal cells. Collectively these results suggest that Di12 gene expression is indeed associated with advanced and aggressive disease, particularly IDCS.

Moreover, random measurement of serum Di12 protein levels indicates that gene expression is significantly increased if IDCs are accompanied by regional lymph node involvement, and most highly elevated if distant metastases are present. Since the predicted Di12 protein lacks a signal sequence, the observed serological circulation Of Di12 protein, could be linked to the malignant invasiveness of IDC associated disease. The data derived from clinical specimen shows that the Di12 gene product is a useful prognostic marker for invasive ductal carcinomas. Since the IDC constitutes more than 70 percent of routine clinical specimens, a positive marker for IDC could be useful in the diagnosis and management of patients after primary resection and could also identify, at an early stage, those women who might benefit from a more aggressive therapeutic protocol.

8. DEPOSIT OF MICROORGANISMS

*E. coli* strain DH5, containing a clone of cDNA encoding Di12, pBSDi12, was deposited on March 20, 1998 with the American Type Culture Collection (ATCC), 10801 University Boulevard, Manassas, Va. 20110–2209, under the provisions of the Budapest Treaty on the International Recognition of the Deposit of Microorganism for the Purpose of Patent Procedures, and bears the ATCC number 209684.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from he foregoing description and accompanying drawings. Such modifications are intended to fall within the scope of the appended claims.

What is claimed is:

1. An isolated nucleic acid molecule comprising:
    (a) a nucleotide sequence that encodes a polypeptide consisting of the amino acid sequence of SEQ ID NO: 2; or
    (b) the complement of the nucleotide sequence of (a).

2. An isolated nucleic acid molecule comprising the nucleotide sequence of SEQ ID NO: 1.

3. An isolated nucleic acid molecule of claim 1, which is cDNA.

4. An isolated nucleic acid molecule of claim 1, which is RNA.

5. An isolated nucleic acid probe that comprises a label and (a) a nucleotide sequence that encodes a polypeptide consisting essentially of the amino acid sequence of SEQ ID NO: 2, or (b) the complement of (a).

6. An isolated nucleic acid molecule comprising a first nucleotide sequence that encodes a polypeptide consisting essentially of the amino acid sequence of SEQ ID NO: 2, linked uninterrupted by stop codons to a second nucleotide sequence that encodes a heterologous protein or peptide.

7. A recombinant vector comprising the nucleotide sequence of claim 1, 2, 3, 5, or 6.

8. An expression vector comprising the nucleotide sequence of claim 1, 2, 3, 5, or 6 operatively associated with a regulatory nucleotide sequence containing transcriptional and translational regulatory information that controls expression of the nucleotide sequence in a host cell.

9. A genetically engineered host cell comprising the nucleotide sequence of claim 1, 2, 3, 5, or 6.

10. A genetically engineered host cell comprising the nucleotide sequence of claim 1, 2, 3, 5, or 6 operatively associated with a regulatory nucleotide sequence containing transitional and translational regulatory information that controls expression of the nucleotide sequence in the host cell.

11. The genetically engineered host cell of claim 10 in which the host cell is prokaryotic.

12. The genetically engineered host cell of claim 10 in which the host cell is eukaryotic.

13. The microorganism deposit of E. coli DH5 containing the plasmid pBS-Di12 bearing American Type Culture Collection Deposit Accession No. 209684.

14. A delivery complex comprising the nucleic acid molecule of claim 1 and a targeting agent.

15. The delivery complex of claim 14, wherein the targeting agent is selected from the group consisting of: a sterol, a lipid, a virus and a target cell specific binding agent.

16. A delivery complex comprising the expression vector of claim 8 and a targeting agent.

17. The delivery complex of claim 16, wherein the targeting agent is selected from the group consisting of: a sterol, a lipid, a virus and a target cell specific binding agent.

18. The delivery complex of claim 16, wherein the targeting agent is selected from the group consisting of a recombinant adenovirus, a recombinant adeno-associated virus, a recombinant retrovirus, a recombinant herpes simplex virus, and a recombinant vaccinia virus.

19. A method for detecting the presence of a nucleic acid molecule of claim 1 in a sample comprising:
    (a) contacting the sample with a nucleic acid probe capable of specifically hybridizing to at least a portion of the nucleic acid molecule of claim 1 under hybridizing conditions; and
    (b) comparing the hybridization of the probe to the nucleic acid molecules of the sample relative to the hybridization of the probe to a control that does not comprise the nucleic acid molecule of claim 1,
    whereby an increase in hybridization in the sample indicates the presence of the nucleic acid molecule of claim 1.

20. A method for detecting the presence of the nucleic acid molecule of claim 1 in a sample comprising:
    (a) contacting the sample with nucleic acid primers capable of specifically binding to at least a portion of the nucleic acid molecule of claim 1 under hybridizing conditions;
    (b) selectively amplifying in the sample of (a) at least a portion of the nucleic acid molecule of claim 1 and;

(c) detecting the amplified nucleic acid molecule of (b), whereby the presence of the amplified nucleic acid molecule of (b) in the sample and not in a control indicates the presence of the nucleic acid molecule of claim 1 in the sample, wherein said control does not comprise the nucleic acid of claim 1 and has been amplified selectively with the nucleic acid primer of (a).

21. A kit comprising the nucleic acid probe of claim 5 and at least one reagent suitable for detecting the presence of a nucleic acid molecule encoding Di12.

22. A method of making a Di12 polypeptide comprising the steps of:

(a) culturing the genetically engineered host cell of claim 11 in an appropriate culture medium to produce Di12 polypeptide; and (b) isolating the Di12 polypeptide.

23. A method of making a Di12 polypeptide comprising the steps of:

(a) culturing the genetically engineered host cell of claim 12 in an appropriate culture medium to produce Di12 polypeptide; and (b) isolating the Di12 polypeptide.

* * * * *

SEQUENCE LISTING

```
<160> NUMBER OF SEQ ID NOS:  16

<210> SEQ ID NO 1
<211> LENGTH: 1374
<212> TYPE: DNA
<213> ORGANISM: Homo sapiens
<220> FEATURE:
<221> NAME/KEY: CDS
<222> LOCATION: (149)...(1165)

<400> SEQUENCE: 1
gggtggagac ttccaagcgt cacttaacca agccgcagtc atcgctggtg gtacatcaaa        60
agacattaac ggacttgctg acgtagccaa caaaatgggt gctgacctgc ctttaagcgc       120
tggtgctgct gcgaaagcta tggtagcc atg gct cgt gac gga gcg tct atc        172
                                Met Ala Arg Asp Gly Ala Ser Ile
                                  1               5
```

-continued

```
aag aca att aaa tca gag ttc cca gct att gcg caa gct gca acg gct      220
Lys Thr Ile Lys Ser Glu Phe Pro Ala Ile Ala Gln Ala Ala Thr Ala
    10              15                  20 gct ggt gct gat ttg cag caa aca gcg tca gtt gtt caa caa tcg atg      268
Ala Gly Ala Asp Leu Gln Gln Thr Ala Ser Val Val Gln Gln Ser Met
25              30                  35                  40 aac atc tgg ggt gat agt att caa agc cca caa cgt gct gct gct gta      316
Asn Ile Trp Gly Asp Ser Ile Gln Ser Pro Gln Arg Ala Ala Ala Val
                45                  50                  55 tta acg caa act gct aac cta tcc aac gcc tca atc gaa gat atg caa      364
Leu Thr Gln Thr Ala Asn Leu Ser Asn Ala Ser Ile Glu Asp Met Gln
            60                  65                  70 cag gct tta gct act atc ggt ggt acg gca cac aac gct ggt atc gac      412
Gln Ala Leu Ala Thr Ile Gly Gly Thr Ala His Asn Ala Gly Ile Asp
        75                  80                  85 atg caa aca acg tct acc gct atc ggt tta ctt act aac cgt ggt ttc      460
Met Gln Thr Thr Ser Thr Ala Ile Gly Leu Leu Thr Asn Arg Gly Phe
    90                  95                  100 agt gct gca caa gcg tca caa gac ttg aac cat gct ttg ttg ctc atg      508
Ser Ala Ala Gln Ala Ser Gln Asp Leu Asn His Ala Leu Leu Leu Met
105                 110                 115                 120 caa gct cca agt gaa aaa gga gct ggt gtg atg cac aat ctc ggt ttg      556
Gln Ala Pro Ser Glu Lys Gly Ala Gly Val Met His Asn Leu Gly Leu
                125                 130                 135 tct atg aca gac gca caa gga aac atg aag ccg tta cca aaa att ttg      604
Ser Met Thr Asp Ala Gln Gly Asn Met Lys Pro Leu Pro Lys Ile Leu
            140                 145                 150 aat gaa att ggt gac gcg aca cgt ggg atg act agt tct gat aaa gca      652
Asn Glu Ile Gly Asp Ala Thr Arg Gly Met Thr Ser Ser Asp Lys Ala
        155                 160                 165 gca gcg ttg aag gct atg ttt ggt act gct ggt atg gct gct att ctt      700
Ala Ala Leu Lys Ala Met Phe Gly Thr Ala Gly Met Ala Ala Ile Leu
    170                 175                 180 cct ttg atg gat agt gtc aag gat aag act aat aat gct acc aca agt      748
Pro Leu Met Asp Ser Val Lys Asp Lys Thr Asn Asn Ala Thr Thr Ser
185                 190                 195                 200 tgg gaa gct ttc acc aaa gaa atg gat aaa gcg tca gga agt acg caa      796
Trp Glu Ala Phe Thr Lys Glu Met Asp Lys Ala Ser Gly Ser Thr Gln
                205                 210                 215 aca gct aca aac ttc cta aaa gat caa gca aac gaa atg cag aaa aac      844
Thr Ala Thr Asn Phe Leu Lys Asp Gln Ala Asn Glu Met Gln Lys Asn
            220                 225                 230 ttg ggt tct aag atc gaa caa gtc ggt ggt aac tgg gaa gca tta agc      892
Leu Gly Ser Lys Ile Glu Gln Val Gly Gly Asn Trp Glu Ala Leu Ser
        235                 240                 245 aac aag gct atg gct gga tct tct ggt gtc act ggt gcg ttc ctt gac      940
Asn Lys Ala Met Ala Gly Ser Ser Gly Val Thr Gly Ala Phe Leu Asp
    250                 255                 260 atg aca aat agc gca tta agt tgg gct ggt tct agt aat agt tca atg      988
Met Thr Asn Ser Ala Leu Ser Trp Ala Gly Ser Ser Asn Ser Ser Met
265                 270                 275                 280 gca cag ttt tca cgt caa atg ctt ggt tta gca cca gct atc ggg cca     1036
Ala Gln Phe Ser Arg Gln Met Leu Gly Leu Ala Pro Ala Ile Gly Pro
                285                 290                 295 gtt gtt act gct ttg ggt gga ttt att acc aac gct ggg aag att act     1084
Val Val Thr Ala Leu Gly Gly Phe Ile Thr Asn Ala Gly Lys Ile Thr
            300                 305                 310 gga ctg gta aaa ggt atg ggt tca gca gtt att ggt gct ggt aag gga     1132
Gly Leu Val Lys Gly Met Gly Ser Ala Val Ile Gly Ala Gly Lys Gly
        315                 320                 325
```

```
atg gtt agt ttt gtt gct ttt ttt ttc ttt gtg taaaaccagt gaatataact   1185
Met Val Ser Phe Val Ala Phe Phe Phe Phe Val
    330                 335 aaagtgttag tggattggat taaaagaaac ttattaggca agaacaggta atgtagttat    1245
ccatgactac ttttaaccat gcagactaat aatattctgg aggtttatag ctcggcacct    1305 tcacctttt tcactggtat ttcatgtaag gcatcaacca ctgtgaaaaa aaaaaaaaa     1365 aaaaaaaaa                                                            1374

<210> SEQ ID NO 2
<211> LENGTH: 339
<212> TYPE: PRT
<213> ORGANISM: Homo sapiens

<400> SEQUENCE: 2

Met Ala Arg Asp Gly Ala Ser Ile Lys Thr Ile Lys Ser Glu Phe Pro
1               5                   10                  15

Ala Ile Ala Gln Ala Thr Ala Ala Gly Ala Asp Leu Gln Gln Thr
            20                  25                  30

Ala Ser Val Val Gln Gln Ser Met Asn Ile Trp Gly Asp Ser Ile Gln
        35                  40                  45

Ser Pro Gln Arg Ala Ala Ala Val Leu Thr Gln Thr Ala Asn Leu Ser
    50                  55                  60

Asn Ala Ser Ile Glu Asp Met Gln Gln Ala Leu Ala Thr Ile Gly Gly
65                  70                  75                  80

Thr Ala His Asn Ala Gly Ile Asp Met Gln Thr Thr Ser Thr Ala Ile
                85                  90                  95

Gly Leu Leu Thr Asn Arg Gly Phe Ser Ala Ala Gln Ala Ser Gln Asp
            100                 105                 110

Leu Asn His Ala Leu Leu Leu Met Gln Ala Pro Ser Glu Lys Gly Ala
        115                 120                 125

Gly Val Met His Asn Leu Gly Leu Ser Met Thr Asp Ala Gln Gly Asn
    130                 135                 140

Met Lys Pro Leu Pro Lys Ile Leu Asn Glu Ile Gly Asp Ala Thr Arg
145                 150                 155                 160

Gly Met Thr Ser Ser Asp Lys Ala Ala Ala Leu Lys Ala Met Phe Gly
                165                 170                 175

Thr Ala Gly Met Ala Ala Ile Leu Pro Leu Met Asp Ser Val Lys Asp
            180                 185                 190

Lys Thr Asn Asn Ala Thr Thr Ser Trp Glu Ala Phe Thr Lys Glu Met
        195                 200                 205

Asp Lys Ala Ser Gly Ser Thr Gln Thr Ala Thr Asn Phe Leu Lys Asp
    210                 215                 220

Gln Ala Asn Glu Met Gln Lys Asn Leu Gly Ser Lys Ile Glu Gln Val
225                 230                 235                 240

Gly Gly Asn Trp Glu Ala Leu Ser Asn Lys Ala Met Ala Gly Ser Ser
                245                 250                 255

Gly Val Thr Gly Ala Phe Leu Asp Met Thr Asn Ser Ala Leu Ser Trp
            260                 265                 270

Ala Gly Ser Ser Asn Ser Ser Met Ala Gln Phe Ser Arg Gln Met Leu
        275                 280                 285

Gly Leu Ala Pro Ala Ile Gly Pro Val Val Thr Ala Leu Gly Gly Phe
    290                 295                 300

Ile Thr Asn Ala Gly Lys Ile Thr Gly Leu Val Lys Gly Met Gly Ser
305                 310                 315                 320
```

Ala Val Ile Gly Ala Gly Lys Gly Met Val Ser Phe Val Ala Phe Phe
            325                 330                 335

Phe Phe Val

<210> SEQ ID NO 3
<211> LENGTH: 17
<212> TYPE: DNA
<213> ORGANISM: Artificial Sequence
<220> FEATURE:
<223> OTHER INFORMATION: Oligonucleotide

<400> SEQUENCE: 3
catggctacc atagctt                                                17

<210> SEQ ID NO 4
<211> LENGTH: 24
<212> TYPE: DNA
<213> ORGANISM: Artificial Sequence
<220> FEATURE:
<223> OTHER INFORMATION: Oligonucleotide

<400> SEQUENCE: 4
catggctacc atagctttcg cagc                                        24

<210> SEQ ID NO 5
<211> LENGTH: 31
<212> TYPE: DNA
<213> ORGANISM: Artificial Sequence
<220> FEATURE:
<223> OTHER INFORMATION: Oligonucleotide

<400> SEQUENCE: 5
catggctacc atagctttcg cagcagcacc a                                31

<210> SEQ ID NO 6
<211> LENGTH: 38
<212> TYPE: DNA
<213> ORGANISM: Artificial Sequence
<220> FEATURE:
<223> OTHER INFORMATION: Oligonucleotide

<400> SEQUENCE: 6
catggctacc atagctttcg cagcagcacc agcgctta                         38

<210> SEQ ID NO 7
<211> LENGTH: 34
<212> TYPE: DNA
<213> ORGANISM: Artificial Sequence
<220> FEATURE:
<223> OTHER INFORMATION: Oligonucleotide

<400> SEQUENCE: 7
agccatggct accatagctt tcgcagcagc acca                             34

<210> SEQ ID NO 8
<211> LENGTH: 35
<212> TYPE: DNA
<213> ORGANISM: Artificial Sequence
<220> FEATURE:
<223> OTHER INFORMATION: Oligonucleotide

<400> SEQUENCE: 8
ggctaccata gctttcgcag cagcaccagc gctta                            35

```
<210> SEQ ID NO 9
<211> LENGTH: 16
<212> TYPE: DNA
<213> ORGANISM: Artificial Sequence
<220> FEATURE:
<223> OTHER INFORMATION: Oligonucleotide

<400> SEQUENCE: 9
tttcgcagca gcacca                                                   16

<210> SEQ ID NO 10
<211> LENGTH: 33
<212> TYPE: RNA
<213> ORGANISM: Artificial Sequence
<220> FEATURE:
<223> OTHER INFORMATION: Hammerhead ribozyme
<221> NAME/KEY: modified_base
<222> LOCATION: all "n" positions
<223> OTHER INFORMATION: n=a, c, g, or u

<400> SEQUENCE: 10
caucaaagcn gnnnnnncng agnagucggc uac                                33

<210> SEQ ID NO 11
<211> LENGTH: 33
<212> TYPE: RNA
<213> ORGANISM: Artificial Sequence
<220> FEATURE:
<223> OTHER INFORMATION: Hammerhead ribozyme
<221> NAME/KEY: modified_base
<222> LOCATION: all "n" positions
<223> OTHER INFORMATION: n=a, c, g, or u

<400> SEQUENCE: 11
acccaaagcn gnnnnnncng agnagucuuu guu                                33

<210> SEQ ID NO 12
<211> LENGTH: 33
<212> TYPE: RNA
<213> ORGANISM: Artificial Sequence
<220> FEATURE:
<223> OTHER INFORMATION: Hammerhead ribozyme
<221> NAME/KEY: modified_base
<222> LOCATION: all "n" positions
<223> OTHER INFORMATION: n=a, c, g, or u

<400> SEQUENCE: 12
ucgcaaagcn gnnnnnncng agnaguccag cac                                33

<210> SEQ ID NO 13
<211> LENGTH: 33
<212> TYPE: RNA
<213> ORGANISM: Artificial Sequence
<220> FEATURE:
<223> OTHER INFORMATION: Hammerhead ribozyme
<221> NAME/KEY: modified_base
<222> LOCATION: all "n" positions
<223> OTHER INFORMATION: n=a, c, g, or u

<400> SEQUENCE: 13
uaccaaagcn gnnnnnncng agnagucagc uuu                                33

<210> SEQ ID NO 14
<211> LENGTH: 20
<212> TYPE: DNA
<213> ORGANISM: Artificial Sequence
<220> FEATURE:
<223> OTHER INFORMATION: Primer
```

-continued

```
<400> SEQUENCE: 14
cggctgctgg tgctgatttg                                                    20

<210> SEQ ID NO 15
<211> LENGTH: 20
<212> TYPE: DNA
<213> ORGANISM: Artificial Sequence
<220> FEATURE:
<223> OTHER INFORMATION: Antisense Primer

<400> SEQUENCE: 15
ccacgtgtcg cgtcaccaat                                                    20

<210> SEQ ID NO 16
<211> LENGTH: 12
<212> TYPE: PRT
<213> ORGANISM: Homo sapiens

<400> SEQUENCE: 16

Met Ala Arg Asp Gly Ala Ser Ile Lys Thr Ile Lys
 1               5                  10
```